(12) United States Patent
Mccoll et al.

(10) Patent No.: US 9,718,887 B2
(45) Date of Patent: Aug. 1, 2017

(54) METHODS AND PRODUCTS FOR PREVENTING AND/OR TREATING METASTATIC CANCER

(71) Applicants: Adelaide Research & Innovation Pty Ltd, Adelaide (AU); Peter MacCallum Cancer Institute, East Melbourne, Victoria (AU)

(72) Inventors: Shaun Reuss Mccoll, Myrtle Bank (AU); Ian Comerford, Glenalta (AU); Yuka Harata-Lee, Greenwith (AU); Mark Smyth, Kelvin Grove (AU)

(73) Assignees: Adelaide Research & Innovation PTY LTD, South Australia (AU); Peter Maccallum Cancer Institute, Victoria (AU)

( * ) Notice: Subject to any disclaimer, the term of this patent is extended or adjusted under 35 U.S.C. 154(b) by 0 days.

(21) Appl. No.: 14/426,534

(22) PCT Filed: Sep. 6, 2013

(86) PCT No.: PCT/AU2013/001014
§ 371 (c)(1),
(2) Date: Mar. 6, 2015

(87) PCT Pub. No.: WO2014/036608
PCT Pub. Date: Mar. 13, 2014

(65) Prior Publication Data
US 2015/0291698 A1    Oct. 15, 2015

(30) Foreign Application Priority Data

Sep. 6, 2012  (AU) .................................. 2012903874

(51) Int. Cl.
| | |
|---|---|
| A61K 39/395 | (2006.01) |
| A61K 39/00 | (2006.01) |
| C12N 15/11 | (2006.01) |
| C07K 16/30 | (2006.01) |
| A61K 31/7105 | (2006.01) |
| C07K 16/28 | (2006.01) |
| C12N 15/113 | (2010.01) |
| G01N 33/50 | (2006.01) |

(52) U.S. Cl.
CPC ...... *C07K 16/3053* (2013.01); *A61K 31/7105* (2013.01); *C07K 16/2866* (2013.01); *C07K 16/30* (2013.01); *C12N 15/1138* (2013.01); *G01N 33/5011* (2013.01); *A61K 2039/505* (2013.01); *C07K 2317/34* (2013.01); *C07K 2317/73* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 6,699,677 B1 | 3/2004 | Schall et al. | |
| 6,835,547 B1 * | 12/2004 | Gosling et al. | ................ 435/7.2 |
| 2003/0186889 A1 | 10/2003 | Forssmann et al. | |
| 2004/0146926 A1 | 7/2004 | Gosling et al. | |
| 2005/0176073 A1 | 8/2005 | Wang et al. | |
| 2005/0239130 A1 | 10/2005 | Gosling et al. | |

FOREIGN PATENT DOCUMENTS

| | | |
|---|---|---|
| WO | 0127146 A3 | 4/2001 |
| WO | 0166598 A2 | 9/2001 |
| WO | 03047420 A3 | 6/2003 |
| WO | 2009142984 A1 | 11/2009 |
| WO | 2012082470 A8 | 6/2012 |

OTHER PUBLICATIONS

Feng et al. 2009. Clin. Can. Res. 15:2962-70.*
Harata-Lee, Y. 'The role of the atypical chemokine receptor CCX-CICR in progression and metastasis of cancer,' Discipline of Microbiology & Immunology, thesis submitted to the University of Adelaide, May 2012. pp. 1-214 [online], [retrieved on Nov. 6, 2013]. Retrieved from the Internet <URL: http://ebooks.adelaide.edu.au/dpsace/bitstream/2440/80399/3/02whole.pdf.
Takatsuka S, et al. 'Generation of a Panel of monoclonal antibodies against atypical chemokine receptor CCX-CKR by DNA immunization,' Journal of Pharmacological and Toxicological Methods, (2011) vol. 63 pp. 250-257. Abstract; p. 265 col. 2; p. 251 cols. 1-2; p. 257 col. 1; pp. 255-256.

* cited by examiner

*Primary Examiner* — Shulamith H Shafer
(74) *Attorney, Agent, or Firm* — McAfee & Taft

(57) ABSTRACT

The present disclosure relates to the prevention and/or treatment of metastatic cancer. Certain example embodiments of the present disclosure provide a method for preventing and/or treating a metastatic cancer in a subject. The method comprises administering to the subject a therapeutically effective amount of an inhibitor of a chemokine receptor CCX-CKR.

8 Claims, 7 Drawing Sheets

METHODS AND PRODUCTS FOR PREVENTING AND/OR TREATING METASTATIC CANCER

PRIORITY CLAIM

This application claims priority to Australian provisional patent application number 2012903874 filed on 6 Sep. 2012, the contents of which is hereby incorporated by reference.

FIELD

The present disclosure relates to methods and products for preventing and/or treating metastatic cancer.

BACKGROUND

Metastatic cancer, or metastatic disease, is the spread of a cancer from one organ to another organ or another site in a subject. Metastasis is a complex series of biological steps in which cancerous cells leave an original site and migrate to another site in a subject via a number of different possible routes, such as via the bloodstream, the lymphatic system, or by direct extension.

Once a cancer has metastasized, the treatment of metastatic cancer relies on the same traditional techniques to treat primary cancer, such as radiosurgery, chemotherapy, radiation therapy and surgery, or a combination of these interventions. In many cases, however, the treatment options that are currently available are not able to cure the metastatic cancer, although metastatic testicular cancer and thyroid cancer are notable exceptions.

Metastatic cancer is also of particular concern as the incidence of some cancers, such as breast cancer or melanoma, remains high in younger people resulting in a profound effect on the number of productive years lost due to the illness.

Melanoma, for example, is a cancer that has a very high incidence and mortality rate. In some countries, melanoma is the most common type of cancer in young adults. The mean age at diagnosis of melanoma is around 50 years, which is 10-15 years earlier than the commoner diagnoses of prostate, bowel, and lung cancer. Therefore, melanoma is second only to breast cancer in the number of productive years lost.

The 15-year survival rates for localised melanoma exceed 50%, but fall to 30% when there is nodal involvement, and to less than 2% when systemic involvement is evident. Metastatic melanoma is essentially incurable, and as such treatment of melanoma places a high emphasis on preventing metastasis of the primary cancer.

Single-agent dacarbazine chemotherapy, with modest response rates of 15-20%, remains the standard of care for treatment of metastatic melanoma as no combination chemotherapy or biochemotherapy has demonstrated improved overall survival in phase III randomised controlled trials. For example, while some proposed vaccine biotherapies have targeted the immune response as a means to preventing and/or treating melanoma, none of these biotherapies produces response or survival rates higher than that of chemotherapy.

Metastatic breast cancer usually occurs several years after resection of the primary breast cancer. Metastatic breast cancer cells frequently differ from the preceding primary breast cancer in properties and may often develop resistance to several lines of previous treatment and acquired increased metastatic potential. The prognosis of metastatic breast cancer is often poor, as distant metastases are the cause of about 90% of deaths due to breast cancer.

It should also be added that an additional complication with respect to the treatment of both primary and metastatic cancers is that treatment regimes involving standard chemotherapeutic agents are known to have variable and unpredictable effects, including efficacy and the extent of undesired side effects.

Accordingly, there is a need to provide improved methods and/or products to address one or more problems in the prevention and/or treatment of metastatic cancer and/or to provide one or more advantages.

SUMMARY

The present disclosure relates to the prevention and/or treatment of metastatic cancer.

Certain embodiments of the present disclosure provide a method of preventing and/or treating metastatic cancer in a subject, the method comprising administering to the subject a therapeutically effective amount of an inhibitor of a chemokine receptor CCX-CKR.

Certain embodiments of the present disclosure provide use of an inhibitor of a chemokine receptor CCX-CKR in the preparation of a medicament for preventing and/or treating metastatic cancer in a subject.

Certain embodiments of the present disclosure provide a method of preventing and/or treating metastasis of a cancer in a subject, the method comprising administering to the subject a therapeutically effective amount of an inhibitor of a chemokine receptor CCX-CKR.

Certain embodiments of the present disclosure provide a method for reducing metastasis of a cancer in a subject, the method comprising administering to the subject a therapeutically effective amount of an inhibitor of a chemokine receptor CCX-CKR.

Certain embodiments of the present disclosure provide a method for reducing growth of a metastatic cancer in a subject, the method comprising administering to the subject a therapeutically effective amount of an inhibitor of a chemokine receptor CCX-CKR.

Certain embodiments of the present disclosure provide a method of inducing an immune response to a metastatic cancer in a subject, the method comprising administering to the subject a therapeutically effective amount of an inhibitor of a chemokine receptor CCX-CKR.

Certain embodiments of the present disclosure provide a pharmaceutical composition comprising a therapeutically effective amount of an inhibitor of a chemokine receptor CCX-CKR and one or more of a pharmaceutically acceptable excipient, vehicle and/or additive.

Certain embodiments of the present disclosure provide an antibody to chemokine receptor CCX-CKR and/or an antigen binding fragment thereof, wherein the antibody and/or the antigen binding fragment thereof inhibits a metastatic cancer.

Certain embodiments of the present disclosure provide an antibody that binds to an extracellular region of a chemokine receptor CCX-CKR and/or an antigen binding fragment of the antibody.

Certain embodiments of the present disclosure provide an antibody raised to an epitope on an extracellular region of a chemokine receptor CCX-CKR and/or an antigen binding fragment of the antibody.

Certain embodiments of the present disclosure provide an antibody that binds to one or more amino acids or an epitope located in one or more of the following regions of a human chemokine receptor CCX-CKR: amino acids 1 to 42, amino acids 109 to 113, amino acids 176 to 201, and amino acids 262 to 289, or an equivalent region of the receptor in another species.

Certain embodiments of the present disclosure provide an antibody raised against a polypeptide comprising all or part of one or more of polypeptide sequences SEQ ID NOs. 5 to 24, and/or a variant of any of the aforementioned polypeptide sequences.

Certain embodiments of the present disclosure provide a method of identifying an agent capable of inhibiting metastasis of a cancer, the method comprising:
  identifying a test agent that modulates chemokine receptor CCX-CKR activity;
  determining the ability of the test agent to inhibit metastasis of a cancer; and
  identifying the test agent as an agent capable of inhibiting metastasis of a cancer.

A non-naturally occurring polypeptide, an isolated polypeptide or a synthetic polypeptide, the polypeptide comprising an amino acid sequence of one or more of polypeptide sequences SEQ ID NOs. 5 to 24, and/or a variant or a fragment of any of the aforementioned polypeptide sequences.

Certain embodiments of the present disclosure provide a non-naturally occurring or synthetic nucleic acid comprising one or more nucleic sequences selected from SEQ ID NOs 1 to 4, the complement of any of the aforementioned nucleic acid sequences, a RNA equivalent of any of the aforementioned nucleic acid sequences, a modified form of the aforementioned nucleic acid sequences and/or a variant or fragment of any of the aforementioned nucleic acid sequences.

Certain embodiments of the present disclosure provide a small interfering RNA to a chemokine receptor CCX-CKR, wherein the small interfering RNA comprises one or more nucleic sequences selected from SEQ ID NOs 1 to 4, the complement of any of the aforementioned nucleic acid sequences, a RNA equivalent of any of the aforementioned nucleic acid sequences, a modified form of the aforementioned nucleic acid sequences and/or a variant or fragment of any of the aforementioned nucleic acid sequences.

Other embodiments are disclosed herein.

BRIEF DESCRIPTION OF THE FIGURES

Certain embodiments are illustrated by the following figures. It is to be understood that the following description is for the purpose of describing particular embodiments only and is not intended to be limiting with respect to the description.

DETAILED DESCRIPTION

Figure 1:
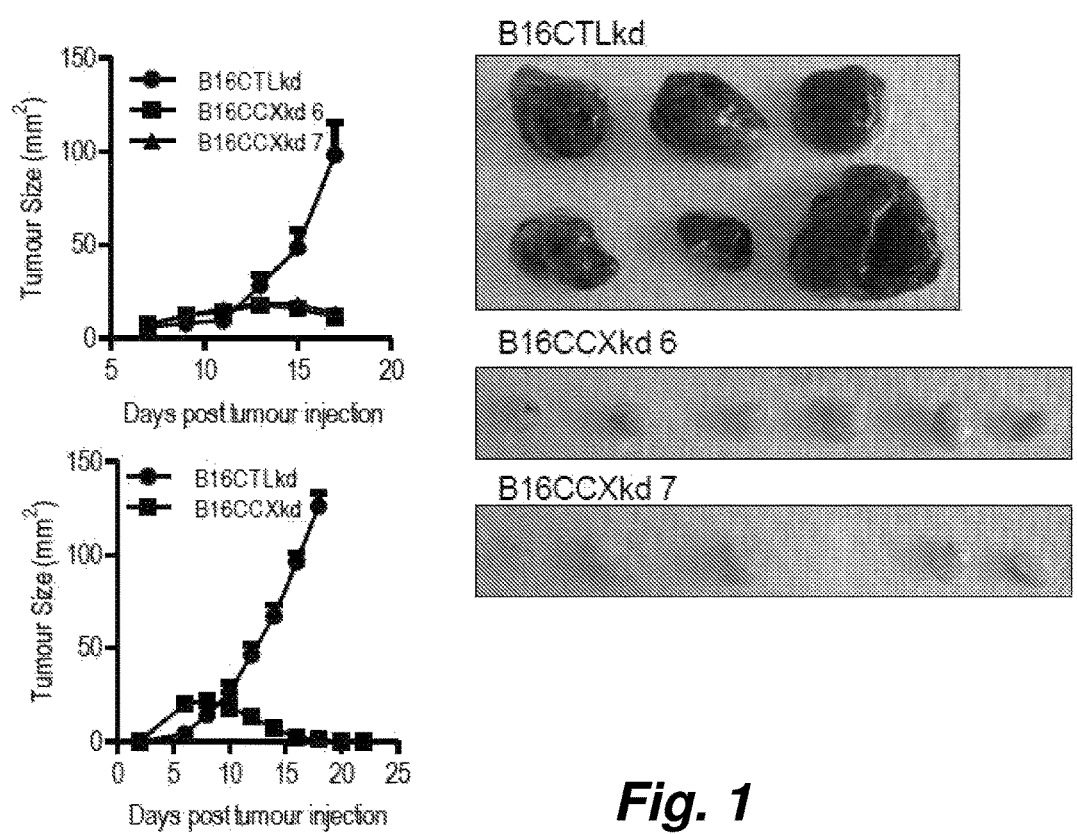
FIG. 1 shows RNAi of CCX-CKR in B16 melanoma cells results in complete rejection of melanoma in mice inoculated with the cells.

The present disclosure relates to the prevention and/or treatment of metastatic cancer.

Certain embodiments of the present disclosure are directed to methods and products that have one or more combinations of advantages. For example, some of the advantages of the embodiments disclosed herein include one or more of the following: providing improved efficacy of treatment of a metastatic cancer; providing improved efficacy of treatment for specific types of metastatic cancers; providing a treatment of metastatic cancer that may utilise an immune response; providing a treatment of metastatic cancer that has reduced side effects; providing new products for preventing and/or treating metastatic cancer; providing anti-metastatic cancer products with improved efficacy; providing anti-metastatic cancer agents with improved efficacy for specific types of cancers; providing products that promote an immune response to a metastatic cancer in the subject; providing anti-metastatic products that have reduced side effects; and providing new methods of screening for candidate anti-metastatic agents. Other advantages of certain embodiments of the present disclosure are also disclosed herein.

Certain embodiments of the present disclosure provide a method for preventing and/or treating a metastatic cancer in a subject, the method comprising administering to the subject a therapeutically effective amount of an inhibitor of a chemokine receptor CCX-CKR.

The present disclosure is based, at least in part, on the determination that the inhibition of the activity of chemokine receptor CCX-CKR inhibits growth and metastasis of cancers, such as melanoma cancer and breast cancer. Without being bound by theory, at least part of the effect appears to involve an immune response to the cancer being induced in the subject.

Certain embodiments of the present disclosure provide a method of preventing and/or treating metastasis of a cancer in a subject, the method comprising administering to the subject a therapeutically effective amount of an inhibitor of a chemokine receptor CCX-CKR.

The term "preventing", and related terms such as "prevention" and "prevent", refer to obtaining a desired pharmacologic and/or physiologic effect in terms of arresting or suppressing the appearance of one or more symptoms in the subject.

The term "treatment", and related terms such as "treating" and "treat", refer to obtaining a desired pharmacologic and/or physiologic effect in terms of improving the condition of the subject, ameliorating, arresting, suppressing, relieving and/or slowing the progression of one or more symptoms in the subject, a partial or complete stabilization of the subject, a regression of the one or more symptoms, or a cure of a disease, condition or state in the subject.

In certain embodiments, the metastatic cancer is a metastasis of a solid cancer. In certain embodiments, the metastatic cancer is a metastasis of a carcinoma. In certain embodiments, the metastatic cancer is a metastasis of a sarcoma. In certain embodiments, the metastatic cancer is a metastasis of a lymphoma. In certain embodiments, the metastatic cancer is a metastasis of a germ cell cancer. In certain embodiments, the metastatic cancer is a metastasis of a blastoma. Other metastatic cancers are contemplated.

In certain embodiments, the metastatic cancer is a metastasis of a melanoma, a breast cancer, a prostate cancer, an ovarian cancer, a lung cancer, a colorectal cancer, a gastric cancer, a pancreatic cancer, a bladder cancer, an oesophageal cancer, an urothelial cancer, a non-small cell lung cancer, a head & neck cancer, a testicular cancer, an uterine cancer, a liver cancer, a renal cancer, a stomach cancer, a cerebral tumour, a malignant myeloma, a lymphoproliferative tumour, a haematological cancer, a CML, an AML, or a B-cell lymphoma. Other types of metastatic cancers are contemplated.

In certain embodiments, the metastatic cancer is a metastatic melanoma, breast cancer, prostate cancer, ovarian cancer, or colorectal cancer. In certain embodiments, the metastatic cancer is a metastasis of a melanoma, a breast cancer, a prostate cancer, an ovarian cancer, or a colorectal cancer.

In certain embodiments, the subject is human subject.

In certain embodiments, the subject is a mammalian subject, a livestock animal (such as a horse, a cow, a sheep, a goat, a pig), a domestic animal (such as a dog or a cat) and other types of animals such as monkeys, rabbits, mice and laboratory animals. Veterinary applications of the present disclosure are contemplated. Use of any of the aforementioned animals as animal models is also contemplated.

In certain embodiments, the subject is suffering from a cancer. Examples of cancers are as described herein. In certain embodiments, the subject is suffering from a solid cancer. In certain embodiments, the subject is suffering from a carcinoma. In certain embodiments, the subject is suffering from a sarcoma. In certain embodiments, the subject is suffering from a lymphoma. In certain embodiments, the subject is suffering from a germ cell cancer. In certain embodiments, the subject is suffering from a blastoma. In certain embodiments, the subject is suffering from a haematological cancer. In certain embodiments, the subject is suffering from a melanoma, a breast cancer, a prostate cancer, an ovarian cancer, lung cancer, a colorectal cancer, a gastric cancer, a pancreatic cancer, a bladder cancer, an oesophageal cancer, an urothelial cancer, a non-small cell lung cancer, head & neck cancer, a testicular cancer, an uterine cancer, a liver cancer, a renal cancer, a stomach cancer, a cerebral tumour, a malignant myeloma, a CML, an AML, or a lymphoproliferative tumour. Other types of cancers are contemplated.

In certain embodiments, the subject is susceptible to a cancer. Examples of cancers are as described herein. In certain embodiments, the subject is susceptible to a solid cancer. In certain embodiments, the subject is susceptible to a carcinoma. In certain embodiments, the subject is susceptible to a sarcoma. In certain embodiments, the subject is susceptible to a lymphoma. In certain embodiments, the subject is susceptible to a germ cell cancer. In certain embodiments, the subject is susceptible to a blastoma. In certain embodiments, the subject is susceptible to a haematological cancer. In certain embodiments, the subject is susceptible to a melanoma, a breast cancer, a prostate cancer, an ovarian cancer, lung cancer, a colorectal cancer, a gastric cancer, a pancreatic cancer, a bladder cancer, an oesophageal cancer, an urothelial cancer, a non-small cell lung cancer, head & neck cancer, a testicular cancer, an uterine cancer, a liver cancer, a renal cancer, a stomach cancer, a cerebral tumour, a malignant myeloma, a CML, an AML or a lymphoproliferative tumour. Other types of cancers are contemplated.

In certain embodiments, the subject has an increased risk or likelihood of suffering from a cancer. Examples of cancers are as described herein. In certain embodiments, the subject has an increased risk or likelihood of suffering from a solid cancer. In certain embodiments, the subject has an increased risk or likelihood of suffering from a carcinoma. In certain embodiments, the subject has an increased risk or likelihood of suffering from a sarcoma. In certain embodiments, the subject has an increased risk or likelihood of suffering from a lymphoma. In certain embodiments, the subject has an increased risk or likelihood of suffering from a germ cell cancer. In certain embodiments, the subject has an increased risk or likelihood of suffering from a blastoma. In certain embodiments, the subject has an increased risk or likelihood of suffering from a haematological cancer. In certain embodiments, the subject has an increased risk or likelihood of suffering from a melanoma, a breast cancer, a prostate cancer, an ovarian cancer, lung cancer, a colorectal cancer, a gastric cancer, a pancreatic cancer, a bladder cancer, an oesophageal cancer, an urothelial cancer, a non-small cell lung cancer, head & neck cancer, a testicular cancer, an uterine cancer, a liver cancer, a renal cancer, a stomach cancer, a cerebral tumour, a malignant myeloma, a CML, an AML or a lymphoproliferative tumour. Other types of cancers are contemplated.

In certain embodiments, the subject is not undergoing treatment for a cancer as described herein. In certain embodiments, the subject is undergoing treatment for a cancer as described herein. In certain embodiments, the subject is undergoing chemotherapeutic treatment for a cancer as described herein.

In certain embodiments, the methods as described herein may be used to reduce the growth and/or volume of a metastatic cancer in a subject.

Certain embodiments of the present disclosure provide a method for reducing growth and/or volume of a metastatic cancer in a subject, the method comprising administering to the subject a therapeutically effective amount of an inhibitor of a chemokine receptor CCX-CKR.

In certain embodiments, the weight and/or volume of a tumour associated with the metastatic cancer is reduced upon administration of the inhibitor. Methods for determining tumour weight and/or volume are known, and include for example imaging of a subject to determine these parameters in situ. In certain embodiments, the weight of the tumour associated with the metastatic cancer is reduced by 30% or more, 40% or more, 50% or more, 60% or more, 70% or more, 80% or more, or 90% or more. In certain embodiments, the volume of the tumour associated with the metastatic cancer is reduced by 30% or more, 40% or more, 50% or more, 60% or more, 70% or more, 80% or more, or 90% or more.

In certain embodiments, the weight and/or volume of a tumour associated with the metastatic cancer is reduced upon administration of the inhibitor in combination with one or more other pharmacological agents, such as a chemotherapeutic agent. In certain embodiments, the weight of the tumour associated with the metastatic cancer using such combination treatment is reduced by 30% or more, 40% or more, 50% or more, 60% or more, 70% or more, 80% or more, or 90% or more. In certain embodiments, the volume of the tumour associated with the metastatic cancer is reduced by 30% or more, 40% or more, 50% or more, 60% or more, 70% or more, 80% or more, or 90% or more.

In certain embodiments, the methods as described herein may be used to reduce growth of metastases in a subject. In certain embodiments, growth of metastases in the subject is reduced.

In certain embodiments, the methods as described herein may be used to reduce metastatic load or burden in a subject. In certain embodiments, metastatic load or burden in the subject is reduced.

Certain embodiments of the present disclosure provide a method for reducing metastasis of a cancer in a subject.

Certain embodiments of the present disclosure provide a method for reducing metastasis of a cancer in a subject, the method comprising administering to the subject a therapeutically effective amount of an inhibitor of a chemokine receptor CCX-CKR.

In certain embodiments, the number of metastases is reduced. In certain embodiments, the number of metastases is reduced by 20% or more, 30% or more, 40% or more, 50% or more, 60% or more, 70% or more, 80% or more, or 90% or more. Methods for determining metastatic load or burden are known, and include for example imaging of a subject to determine this parameter in situ.

In certain embodiments, the methods as described herein may be used to reduce the number of metastases in a subject. In certain embodiments, the number of metastases in the subject is reduced.

In certain embodiments, the methods as described herein may be used to induce an immune response to the metastatic cancer in a subject.

In certain embodiments, administering the inhibitor of a chemokine receptor CCX-CKR to the subject induces an immune response to the metastatic cancer in the subject.

Certain embodiments of the present disclosure provide a method of preventing and/or treating a metastatic cancer in a subject, the method comprising administering to the subject a therapeutically effective amount of an inhibitor of a chemokine receptor CCX-CKR and thereby induce an immune response to the metastatic cancer in the subject.

Certain embodiments of the present disclosure provide a method of inducing an immune response to a metastatic cancer in a subject, the method comprising administering to the subject a therapeutically effective amount of an inhibitor of a chemokine receptor CCX-CKR.

In certain embodiments, the methods as described herein may be used to induce anti-tumour $CD4^+$ and/or $CD8^+$ cells in a subject. In certain embodiments, administering the inhibitor of a chemokine receptor CCX-CKR to the subject induces anti-tumour $CD4^+$ and/or $CD8^+$ cells.

The CCX-CKR gene (also referred to as CCRL1 or CCR11) encodes a receptor of the G protein-coupled receptor family, and is a receptor for C-C type chemokines. In humans, the receptor is encoded by the gene with the Genbank accession number AF110640. The equivalent receptor in other species may be determined by a known method. The amino acid sequence of the human receptor has the Genbank accession number AF110640_1. Methods for determining the CCX-CKR gene and receptor in other species are known and include for example nucleic acid and protein alignment programs, such as BLAST.

In certain embodiments, the chemokine receptor CCX-CKR is a human receptor. In certain embodiments, the chemokine receptor CCX-CKR is an animal receptor. In certain embodiments, the chemokine receptor CCX-CKR is a mammalian receptor.

In certain embodiments, the chemokine receptor CCX-CKR is a full length receptor. In certain embodiments, the chemokine receptor CCX-CKR is a part of a receptor. In certain embodiments, the chemokine receptor CCX-CKR is a homolog, paralog or ortholog of a receptor. In certain embodiments, the chemokine receptor CCX-CKR is a variant and/or fragment of the receptor, such as a variant of the receptor arising from an alternatively spliced transcript.

The term "inhibitor" as used herein refers to an agent, treatment, or intervention that results directly or indirectly in a reduction of chemokine receptor CCX-CKR expression, activity or function, including for example a decrease in expression, a decrease in activity, an inhibitory alteration in the timing and/or location of activity, or otherwise provide inhibitory control over activity. Other forms of inhibition are contemplated.

For example, an inhibitor may (i) act directly to alter the activity of a receptor, such as altering the level of expression of the receptor, altering localisation of the receptor, partially or completely removing the gene for the receptor, altering internationalisation of the receptor or altering timing of receptor function; (ii) act to alter the activity of a signalling pathway associated with an receptor; (iii) act to alter the level and/or alter the activity of a ligand that binds to the receptor, such as altering the synthesis of the ligand. In certain embodiments, the inhibitor is a selective inhibitor. In certain embodiments, the inhibitor is a non-selective inhibitor.

Examples of inhibitors include a drug, a small molecule, a protein, a polypeptide, a lipid, a carbohydrate, a nucleic acid, an oligonucleotide, a ribozyme, a biologic, an aptamer, a cofactor, a ligand, a ligand mimetic, a receptor, an enzyme, a kinase, a phosphatase, a cytokine, a growth factor, a metal ion, a chelate, an antisense nucleic acid, an inhibitor RNA, a microRNA, a siRNA, an antibody or antigen binding part thereof, an antibody mimetic, an antagonist, an inhibitor, or a suppressor. Other types of inhibitors are contemplated.

In certain embodiments, the inhibitor comprises a drug, a small molecule, a protein, a polypeptide, a lipid, a carbohydrate, a nucleic acid, an oligonucleotide, a ribozyme, a biologic, an aptamer, a cofactor, a ligand, a ligand mimetic, a receptor, an enzyme, a kinase, a phosphatase, a cytokine, a growth factor, a metal ion, a chelate, an antisense nucleic acid, an inhibitor RNA, a microRNA, a siRNA, an antibody or antigen binding part thereof, an antibody mimetic, an antagonist, an inhibitor, or a suppressor.

The term "activity" as used herein refers to the function of a species and includes, for example, the level, the specificity, the ability to interact (directly and/or indirectly) with and/or modify other species, the ability to signal, and the ability to cause changes (directly and/or indirectly) in other cellular and/or non-cellular events. Examples of modulating the activity of a species include, for example, changes in the level of the species, changes in the localisation of the species, changes in the synthesis and/or degradation rates of the species, changes in the timing of activity, changes in the ability to interact with other species (such as a change in the ability of a ligand and a receptor to interact), changes in the chemical composition of the species, changes in signalling, and changes in cellular and/or non-cellular events affected by the species.

An inhibitor of a chemokine receptor CCX-CKR may be synthesized, produced or obtained commercially.

Certain embodiments of the present disclosure provide use of an inhibitor as described herein in the preparation of a medicament for preventing and/or treating a metastatic cancer in a subject.

In certain embodiments, the inhibitor comprises one or more of a small interfering RNA, an antisense RNA, a ligand for a CCX-CKR, a modification to a ligand for a chemokine receptor CCX-CKR, a gene knockout agent, a gene knockdown agent or an antibody and/or an antigen binding part thereof.

In certain embodiments, the inhibitor comprises one or more of a small interfering RNA to a chemokine receptor CCX-CKR, an antisense RNA to a chemokine receptor CCX-CKR, a ligand for a CCX-CKR, a modification to a ligand for a chemokine receptor CCX-CKR, a gene knockout agent to a chemokine receptor CCX-CKR, a gene knockdown agent to a chemokine receptor CCX-CKR or an antibody and/or an antigen binding part thereof to a chemokine receptor CCX-CKR.

In certain embodiments, the inhibitor is a modulator of ligand binding to a chemokine receptor CCX-CKR. Examples of such inhibitors include a ligand antagonist or an antibody antagonist. In certain embodiments, the inhibitor reduces binding of a ligand to a chemokine receptor CCX-CKR.

In certain embodiments, the inhibitor modulates the binding of a ligand to a chemokine receptor CCX-CKR. In certain embodiments, the inhibitor is a modulator of one or more of CCL25 binding, CCL19 binding and CCL21 binding. In certain embodiments, the inhibitor inhibits the binding of a ligand to a chemokine receptor CCX-CKR. In certain embodiments, the inhibitor is an inhibitor of one or more of CCL25 binding, CCL19 binding and CCL21 binding.

In certain embodiments, the inhibitor modulates the activity of a ligand for a chemokine receptor CCX-CKR. In certain embodiments, the inhibitor is a modulator of one or more of CCL25 activity, CCL19 activity and CCL21 activity. In certain embodiments, the inhibitor is an inhibitor of one or more of CCL25 activity, CCL19 activity and CCL21 activity.

In certain embodiments, the inhibitor modulates the synthesis of a ligand for a chemokine receptor CCX-CKR. In certain embodiments, the inhibitor modulates the synthesis of one or more of CCL25, CCL19 and CCL21. In certain embodiments, the inhibitor inhibits the synthesis of one or more of CCL25, CCL19 and CCL21.

In certain embodiments, the inhibitor modulates the processing of a species that forms a ligand for a chemokine receptor CCX-CKR. In certain embodiments, the inhibitor modulates the processing of precursor of one or more of CCL25, CCL19 and CCL21. In certain embodiments, the inhibitor inhibits the processing of precursor of one or more of CCL25, CCL19 and CCL21.

In certain embodiments, the inhibitor is an inhibitor of a chemokine receptor CCX-CKR expression. Examples of such inhibitors include an antisense RNA to a chemokine receptor CCX-CKR mRNA or a small interfering RNA to a chemokine receptor CCX-CKR.

In certain embodiments, the inhibitor promotes internalisation of a chemokine receptor CCX-CKR.

The term "nucleic acid" as used herein refers to an oligonucleotide or a polynucleotide and includes for example DNA, RNA, DNA/RNA, a variant or DNA and/or RNA (for example a variant of the sugar-phosphate backbone and/or a variant of one or more bases, such as methylation), and may be single stranded, double stranded, non-methylated, methylated or other forms thereof. In certain embodiments, the nucleic acid is a non-naturally occurring nucleic acid, a naturally occurring nucleic acid, a nucleic acid of genomic origin, a mitochondrial nucleic acid, a nucleic acid of cDNA origin (derived from a mRNA), a nucleic acid derived from a virus, a nucleic acid of synthetic origin, a single stranded DNA, a double stranded DNA, an analogue of DNA and/or RNA, and/or a derivative, fragment and/or combination of any of the aforementioned. Examples of derivatives also include nucleic acids that have a blocking group at the 5' and/or 3' ends for example to improve stability, and/or nucleic acids fused to other molecules. Other types of nucleic acids are contemplated. Methods for producing nucleic acids are known and include for example nucleic acids produced by recombinant DNA technology or nucleic acids produced by chemical synthesis.

The term "nucleic acid" as used herein also refers to a specified nucleic acid, or a nucleic acid comprising a nucleotide sequence which is the complement of the nucleic acid, a nucleic acid comprising a nucleotide sequence with greater than 70%, 75%, 80%, 85%, 90% or 95% sequence identity to the specified nucleic acid, or a nucleic acid comprising a nucleotide sequence with greater than 70%, 75%, 80%, 85%, 90% or 95% sequence identity to the complement of the specified nucleic acid. Other levels of sequence identity are contemplated.

In certain embodiments, the inhibitor is an antisense nucleic acid, such as an antisense RNA. In certain embodiments, the inhibitor is a small interfering RNA. In certain embodiments, the inhibitor is a microRNA. Methods for producing and delivering antisense nucleic acids, microRNAs and siRNAs are known. For example, therapeutic nucleic acids for treating cancer are described in "Nucleic Acid Therapeutics in Cancer" 2004 ed. Alan M. Gewirtz, Humana Press Inc.

Certain embodiments of the present disclosure provide a small interfering RNA to a chemokine receptor CCX-CKR.

In certain embodiments, the small interfering RNA comprises a nucleotide sequence of SEQ ID NO. 1, the complement of SEQ ID NO. 1, an RNA equivalent of SEQ ID NO. 1, a modified form of SEQ ID NO.1, and/or a functional variant or functional fragment thereof. The nucleotide sequence of SEQ ID NO. 1 is as follows:

```
                                              (SEQ ID NO. 1)
         5'-TATGCAGATCACTTCGTACTG-3'.
```

In certain embodiments, the small interfering RNA comprises a nucleotide sequence of SEQ ID NO. 2, the complement of SEQ ID NO. 2, an RNA equivalent of SEQ ID NO. 2, a modified form of SEQ ID NO. 2, and/or a functional variant or functional fragment thereof. The nucleotide sequence of SEQ ID NO. 2 is as follows:

```
                                              (SEQ ID NO. 2)
         5'-CCGGCAGTACGAAGTGATCTGCATACTCGAGTATGCAGATC

ACTTCGTACTGTTTTT-3'.
```

In certain embodiments, the small interfering RNA consists of a nucleotide sequence of SEQ ID NO. 1 or SEQ ID NO. 2, the complement of SEQ ID NO. 1 or 2, an RNA equivalent of SEQ ID NO. 1 or 2, a modified form of SEQ ID NO. 1 or 2, and/or a functional variant or functional fragment of the aforementioned nucleotide sequences.

The term "variant" as used herein in reference to a nucleic acid refers to a nucleic acid with 70% or greater, 75% or greater, 80% or greater, 85% or greater, 90% or greater, 95% or greater, 96% or greater, 97% or greater, 98% or greater, or 99% or greater sequence identity with the reference nucleic acid.

In certain embodiments, the small interfering RNA comprises a nucleotide sequence of SEQ ID NO. 3, the complement of SEQ ID NO. 3, an RNA equivalent of SEQ ID NO. 3, a modified form of SEQ ID NO. 3, and/or a functional variant or functional fragment thereof. The nucleotide sequence of SEQ ID NO. 3 is as follows:

```
                                        (SEQ ID NO. 3)
        5'-ATGCGTTTGCTCATATCGCAG-3'.
```

In certain embodiments, the small interfering RNA comprises a nucleotide sequence of SEQ ID NO. 4, the complement of SEQ ID NO. 4, an RNA equivalent of SEQ ID NO. 4, a modified form of SEQ ID NO. 4, and/or a functional variant or functional fragment thereof. The nucleotide sequence of SEQ ID NO. 4 is as follows:

```
                                        (SEQ ID NO. 4)
        5'-CCGGCTGCGATATGAGCAAACGCATCTCGAGATGCGTTTGC

TCATATCGCAGTTTTT-3'.
```

In certain embodiments, the small interfering RNA consists of a nucleotide sequence of SEQ ID NO. 3 or SEQ ID NO. 4, the complement of SEQ ID NO. 3 or 4, an RNA equivalent of SEQ ID NO. 3 or 4, a modified form of SEQ ID NO. 3 or 4, and/or a functional variant or functional fragment of the aforementioned nucleotide sequences.

In certain embodiments, the inhibitor comprises an antibody and/or an antigen binding fragment thereof. In certain embodiments, the inhibitor comprises a neutralising antibody. In certain embodiments, the inhibitor comprises an antagonist antibody.

In certain embodiments, the inhibitor comprises an antibody and/or an antigen binding fragment thereof to a chemokine receptor CCX-CKR. In certain embodiments, the inhibitor comprises a neutralising antibody to a chemokine receptor CCX-CKR. In certain embodiments, the inhibitor comprises an antagonist antibody to a chemokine receptor CCX-CKR. In certain embodiments, the inhibitor comprises an antibody that promotes internalisation of a chemokine receptor CCX-CKR.

The term "antibody" as used herein refers to an immunoglobulin molecule with the ability to bind an antigenic region of another molecule, and includes monoclonal antibodies, polyclonal antibodies, multivalent antibodies, chimeric antibodies, multispecific antibodies, diabodies and fragments of an immunoglobulin molecule or combinations thereof that have the ability to bind to the antigenic region of another molecule with the desired affinity including a Fab, Fab', F(ab')$_2$, Fv, a single-chain antibody (scFv) or a polypeptide that contains at least a portion of an immunoglobulin (or a variant of an immunoglobulin) that is sufficient to confer specific antigen binding, such as a molecule including one or more CDRs.

In this regard, an immunoglobulin is a tetrameric molecule, each tetramer being composed of two identical pairs of polypeptide chains, each pair having one light chain and one heavy chain. The amino-terminal portion of each chain includes a variable region of about 100 to 110 or more amino acids that is primarily responsible for antigen recognition. The carboxy-terminal portion of each chain defines a constant region primarily responsible for effector function. Human light chains are classified as K and λ light chains. Heavy chains are classified as μ, Δ, γ, α, or ε and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. The variable regions of each light/heavy chain pair form the antibody binding site, with the result that an intact immunoglobulin has two binding sites. The variable regions further include hypervariable regions that are directly involved in formation of the antigen binding site. These hypervariable regions are usually referred to as Complementarity Determining Regions (CDR). The intervening segments are referred to as Framework Regions (FR). In both light and heavy chains there are three CDRs (CDR-I to CDR-3) and four FRs (FR-I to FR-4).

In certain embodiments, the antigen-binding fragment comprises a Fab, Fab', F(ab')2, Fd, Fv, a single-chain antibody (scFv), a chimeric antibody, a diabody or a polypeptide that contains at least a portion of an immunoglobulin that is sufficient to confer specific antigen binding.

A Fab fragment is a monovalent fragment consisting of the VL, VH, CL and CH I domains. A F(ab')$_2$ fragment is a bivalent fragment including two Fab fragments linked by a disulphide bridge at the hinge region. A Fd fragment consists of the VH and CH I domains. A Fv fragment consists of the VL and VH domains of a single arm of an antibody. A dAb consists of a VH domain. A single chain antibody (scFv) is an antibody in which VL and VH regions are paired to form a monovalent molecule via a synthetic linker that enable them to be made as a single protein chain. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites.

Antibody fragments that contain specific binding sites may be generated by a known method. Methods for producing antigen-binding fragments or portions of antibodies are known in the art, for example as described in "Antibody Engineering: Methods and Protocols" (2004) ed. by B. K. C. Lo Humana Press, herein incorporated by reference; and "Antibody Engineering: A Practical Approach" (1996) ed. by J. McCafferty, H. R. Hoogenboom and D J. Chriswell Oxford University Press, herein incorporated by reference. For example, F(ab')$_2$ fragments can be produced by pepsin digestion of the antibody molecule, and Fab fragments can be generated by reducing the disulfide bridges of the F(ab')$_2$ fragments. Alternatively, Fab expression libraries may be constructed to allow rapid and easy identification of monoclonal Fab fragments with the desired specificity, as described for example in Huse, W. D. et al. (1989) Science 254: 1275-1281, herein incorporated by reference.

Antibodies may be generated using known methods. For the production of antibodies, various hosts including goats, rabbits, rats, mice, humans, and others, may be immunized by injection with an appropriate antigen. Depending on the host species, various adjuvants may be used to increase an immunological response. Such adjuvants include Freund's adjuvant, mineral gels such as aluminium hydroxide, and surface-active substances such as lysolecithin, pluronic polyols, polyanions, peptides, oil emulsions, keyhole limpet hemocyanin, and dinitrophenol. Adjuvants are commercially available.

In certain embodiments, the antibody is a polyclonal antibody. A polyclonal antibody is a mixture of antibodies having different antigen specificities. Methods for producing and isolating polyclonal antibodies are known. In general, polyclonal antibodies are produced from B-lymphocytes. Typically polyclonal antibodies are obtained directly from an immunized subject, such as an immunized animal.

In certain embodiments, the antibody is a monoclonal antibody. Monoclonal antibodies may be prepared using a technique that provides for the production of antibody molecules by continuous isolated cells in culture. These include, but are not limited to, the hybridoma technique, the human B-cell hybridoma technique, and the EBV-hybridoma technique. Methods for the preparation of monoclonal antibodies include for example Kohler et al. (1975) Nature 256:495-497, herein incorporated by reference; Kozbor et al. (1985) J. Immunol. Methods 81:31-42, herein incorporated by reference; Cote et al. (1983) Proc. Natl. Acad. ScL 80:2026-2030, herein incorporated by reference; and Cole et al. (1984) MoI. Cell Biol. 62: 109-120, herein incorporated by reference.

In certain embodiments, the antibody and/or an antigen binding fragment thereof comprises an isolated antibody. Methods for producing and isolating polyclonal and monoclonal antibodies are known.

In certain embodiments, the antibody as described herein has an isotype selected from the group consisting of IgG1, IgG2a, IgG2b, IgG3, IgM and IgA. Determination of the isotype of an antibody may be by a known method.

In certain embodiments, the antibody and/or an antigen binding fragment thereof is a mouse antibody and/or an antigen binding fragment thereof, a human antibody and/or an antigen binding fragment thereof, or a humanized antibody and/or an antigen binding fragment thereof.

Humanized antibodies, or antibodies adapted for non-rejection by other mammals, may be produced by a suitable method known in the art, including for example resurfacing or CDR grafting. In resurfacing technology, molecular modeling, statistical analysis and mutagenesis are combined to adjust the non-CDR surfaces of variable regions to resemble the surfaces of known antibodies of the target host. Strategies and methods for the resurfacing of antibodies, and other methods for reducing immunogenicity of antibodies within a different host are known, for example as described in U.S. Pat. No. 5,639,641. Humanized forms of the antibodies may also be made by CDR grafting, by substituting the complementarity determining regions of, for example, a mouse antibody, into a human framework domain.

Methods for humanizing antibodies are known. For example, the antibody may be generated as described in U.S. Pat. No. 6,180,370, herein incorporated by reference; WO 92/22653, herein incorporated by reference; Wright et al. (1992) Critical Rev. in Immunol. 12(3,4): 125-168, herein incorporated by reference; and Gu et al. (1997) Thrombosis and Hematocyst 77(4):755-759), herein incorporated by reference.

Humanized antibodies typically have constant regions and variable regions other than the complementarity determining regions (CDRs) derived substantially or exclusively from a human antibody and CDRs derived substantially or exclusively from the non-human antibody of interest.

Techniques developed for the production of "chimeric antibodies", for example the splicing of mouse antibody genes to human antibody genes to obtain a molecule with appropriate antigen specificity and biological activity, may be performed by a suitable method. For example, chimeric antibodies may be produced as described in Morrison, S. L. et al. (1984) Proc. Natl. Acad. ScL 81:6851-6855, herein incorporated by reference; Neuberger, M. S. et al. (1984) Nature 312:604-608, herein incorporated by reference; and Takeda, S. et al. (1985) Nature 314:452-454, herein incorporated by reference.

Immunoassays may be used for screening to identify antibodies and/or antigen binding fragments thereof having the desired specificity. Protocols for competitive binding or immunoradiometric assays using either polyclonal or monoclonal antibodies are known.

Antibody molecules and antigen binding fragments thereof may also be produced recombinantly by methods known in the art, for example by expression in E. coli expression systems. For example, a method for the production of recombinant antibodies is as described in U.S. Pat. No. 4,816,567, herein incorporated by reference. Antigen binding fragments may also be produced by phage display technologies, which are known.

In certain embodiments, the antibody and/or an antigen binding fragment thereof binds to a human chemokine receptor CCX-CKR. In certain embodiments, the antibody and/or an antigen binding fragment thereof binds to a mammalian chemokine receptor CCX-CKR. Methods for assessing the binding of antibodies and/or antigen binding fragments are known In certain embodiments, the antibody and/or antigen binding fragment thereof modulates binding of a ligand to a chemokine receptor CCX-CKR. Determination of the ability of an antibody to modulate ligand binding may be performed by a known method.

In certain embodiments, the antibody and/or the antigen binding fragment thereof binds to a chemokine receptor CCX-CKR. The amino acid sequence of human CCX-CKR is provided by Genbank Accession No. NP_057641.1. The amino acid sequence of a chemokine receptor CCX-CKR from other species are available or may be identified by a person skilled in the art.

In certain embodiments, the antibody and/or the antigen binding fragment thereof binds to an extracellular region of a chemokine receptor CCX-CKR. In certain embodiments, the antibody and/or the antigen binding fragment thereof binds to an epitope in an extracellular region of a chemokine receptor CCX-CKR.

In certain embodiments, the antibody and/or the antigen binding fragment thereof binds to one or more amino acids or an epitope located in one or more of the following regions of the human chemokine receptor CCX-CKR: amino acids 1 to 42, amino acids 109 to 113, amino acids 176 to 201, and amino acids 262 to 289; or an equivalent region of the receptor in another species.

In certain embodiments, the antibody and/or the antibody binding fragment thereof binds to an amino terminal region of the chemokine receptor CCX-CKR. In certain embodiments, the antibody binds to the amino-terminal extracellular region of a chemokine receptor CCX-CKR.

In certain embodiments, the antibody binds to a region comprising one or more amino acids or an epitope located in a region from amino acids 1 to 42 of a chemokine receptor CCX-CKR. In certain embodiments, the antibody binds to one or more amino acids or an epitope located in a region from amino acids 1 to 42 of a chemokine receptor CCX-CKR.

In certain embodiments, the antibody and/or antigen binding fragment thereof binds to one or more amino acids or an epitope in the following polypeptide sequence: CCX-CKR: MALEQNQSTDYYYEENEMNGTYDYSQYELICIKEDVREFAKV (SEQ ID NO. 5) or a variant thereof.

In certain embodiments, the antibody and/or antigen binding fragment thereof binds to one or more amino acids or an epitope in the following polypeptide sequences: MALEQNQSTDYYYEENEMNG (SEQ ID NO. 6); TYDYSQYELICIKEDVREFAK (SEQ ID NO. 7); MALELNQSAEYY (SEQ ID NO. 13); NYTHDYSQYEVI (SEQ ID NO. 14), MALEQNQSTDYY (SEQ ID NO.19), NGTYDYSQYELI (SEQ ID NO.20) or a variant of one of the aforementioned sequences.

In certain embodiments, the antibody binds to a region comprising one or more amino acids or an epitope located in a region from amino acids 100 to 111 of a chemokine receptor CCX-CKR. In certain embodiments, the antibody and/or antigen binding fragment thereof binds to one or more amino acids or an epitope in the following polypeptide sequences: NAVHGWILGKMM (SEQ ID NO. 15), NAVHGWVLGKIM (SEQ ID NO. 21) or a variant thereof.

In certain embodiments, the antibody binds to a region comprising one or more amino acids or an epitope located in a region from amino acids 109 to 113 of a chemokine receptor CCX-CKR. In certain embodiments, the antibody and/or antigen binding fragment thereof binds to one or more amino acids or an epitope in the following polypeptide sequence: KIMCK (SEQ ID NO. 8) or a variant thereof.

In certain embodiments, the antibody binds to a region comprising one or more amino acids or an epitope located in a region from amino acids 176 to 201 of a chemokine receptor CCX-CKR. In certain embodiments, the antibody binds to a region comprising one or more amino acids or an epitope located in a region from amino acids 180 to 191 of a chemokine receptor CCX-CKR. In certain embodiments, the antibody binds to a region comprising one or more amino acids or an epitope located in a region from amino acids 186 to 197 of a chemokine receptor CCX-CKR.

In certain embodiments, the antibody and/or antigen binding fragment thereof binds to one or more amino acids or an epitope in the following polypeptide sequence: YTVNDNARCIPIFPRYLGTSMKALIQ (SEQ ID NO. 9) or a variant thereof. In certain embodiments, the antibody and/or antigen binding fragment thereof binds to one or more amino acids or an epitope in the following polypeptide sequences: QNARCTPIFPHH (SEQ ID NO. 16), DNARCIPIFPRY (SEQ ID NO.22) or a variant thereof. In certain embodiments, the antibody and/or antigen binding fragment thereof binds to one or more amino acids or an epitope in the following polypeptide sequences: PIFPHHLGTSLK (SEQ ID NO. 17), PIFPRYLGTSMK (SEQ ID NO. 23) or a variant thereof.

In certain embodiments, the antibody binds to one or more amino acids or an epitope located in a region from amino acids 262 to 289 of a chemokine receptor CCX-CKR. In certain embodiments, the antibody binds to one or more amino acids or an epitope located in a region from amino acids 276 to 287 of a chemokine receptor CCX-CKR.

In certain embodiments, the antibody and/or antigen binding fragment thereof binds to one or more amino acids or an epitope in the following polypeptide sequence: CRAIDIIYSLITSCNMSKRMDIAIQVTE (SEQ ID NO. 10) or a variant thereof. In certain embodiments, the antibody and/or antigen binding fragment thereof binds to one or more amino acids or an epitope in the following polypeptide sequences: DMSKRMDVAIQV (SEQ ID NO. 18), NMSKRMDIAIQV (SEQ ID NO.24) or a variant thereof.

In certain embodiments, the antibody and/or the antigen binding fragment thereof binds to one or more amino acids or an epitope located in one or more of the following regions of the human chemokine receptor CCX-CKR: amino acids 1 to 42, amino acids 109 to 113, amino acids 176 to 201, and amino acids 262 to 289, or an equivalent region of the receptor in another species.

In certain embodiments, the antibody and/or the antigen binding fragment thereof binds to one or more amino acids or an epitope in one or more of polypeptide sequences SEQ ID NOs 5 to 24.

Certain embodiments of the present disclosure provide a non-naturally occurring polypeptide, an isolated polypeptide or a synthetic polypeptide of a polypeptide as described herein.

Certain embodiments of the present disclosure provide an antibody raised against polypeptides as described herein. Certain embodiments of the present disclosure provide a method of producing an antibody by raising the antibody to a polypeptide as described herein.

Certain embodiments of the present disclosure provide a non-naturally occurring polypeptide, an isolated polypeptide or a synthetic polypeptide, the polypeptide comprising an amino acid sequence selected from one or more of SEQ ID NOs. 5 to 24, and/or a variant or fragment thereof.

Certain embodiments of the present disclosure provide a non-naturally occurring, an isolated or a synthetic polypeptide consisting of an amino acid sequence selected from one or more of SEQ ID NOs.5 to 24, or a variant or fragment thereof.

Certain embodiments of the present disclosure provide an antibody raised against a polypeptide comprising an amino acid sequence selected from one or more of SEQ ID NOs. 5 to 24, or a variant or fragment thereof. Certain embodiments of the present disclosure provide an antibody raised against an epitope present in one or more of SEQ ID NOs.5 to 24, or a variant or fragment thereof. Certain embodiments provide an antibody raised against an epitope present in a polypeptide sequence as described herein.

The term "polypeptide" as used herein refers to oligo- and poly-peptides and refers to substances comprising for example two or more, 3 or more, 4 or more, 5 or more, 6 or more, 7 or more, 8 or more, 9 or more, 10 or more, 20 or more, 30 or more, 40 or more or 50 or more amino acids joined covalently by peptide bonds. The term "protein" typically refers to large polypeptide, but in general the terms "polypeptides" and "proteins" are synonyms and are used interchangeably herein.

In certain embodiments, the nucleic acids and polypeptides described herein are isolated. The term "isolated" refers to a nucleic acid or a polypeptide that has been separated from its natural environment. For example, an isolated nucleic acid or polypeptide may be in a substantially purified state, being substantially free of other substances with which it is associated in nature or in vivo.

Polypeptides described herein may be isolated from biological samples (such as tissue or cell homogenates), may be expressed recombinantly in a multiplicity of pro- or eukaryotic expression systems, or synthesized by known chemical means.

The term "variant" of a polypeptide or of an amino acid sequence refers to one or more of amino acid insertion variants, amino acid deletion variants, amino acid substitution variants, and amino acid modification variants (natural and/or synthetic).

For example, amino acid insertion variants may comprise amino- and/or carboxy-terminal fusions and also insertions of single or two or more amino acids in a particular amino acid sequence. In the case of amino acid sequence variants having an insertion, one or more amino acid residues may be inserted into a particular site in an amino acid sequence, although random insertion with appropriate screening of the resulting product is also possible.

Amino acid deletion variants are characterized by the removal of one or more amino acids from the sequence. Amino acid substitution variants are characterized by at least one residue in the sequence being removed and another residue being inserted in its place. Amino acid changes in variants may be non-conservative and/or conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

In certain embodiments, the degree of similarity, for example identity, between a given amino acid sequence and an amino acid sequence which is a variant of said given amino acid sequence will be at least 70%, at least 80%, at least 85%, even more least 90% or at least 95%, 96%, 97%, 98% or 99%. The degree of similarity or identity may be for a region of at least about 10, at least 20, at least a 40, at least 60, at least 80, at least 100, at least 120, at least 140, at least 160, or at least 200 amino acids.

The polypeptides and amino acid variants described herein may be readily prepared with the aid of known peptide synthesis techniques such as, for example, by solid phase synthesis and similar methods or by recombinant DNA manipulation. The manipulation of DNA sequences for preparing proteins and peptides having substitutions, insertions or deletions, is described in detail in Sambrook, J, Fritsch, E. F. and Maniatis, T. Molecular Cloning: A Laboratory Manual 2nd. ed. Cold Spring Harbor Laboratory Press, New York. (1989), herein incorporated by reference, and Ausubel et al., Current Protocols in Molecular Biology (2011), John Wiley & Sons, Inc., herein incorporated by reference.

The term "derivatives" of polypeptides refer to modified forms of polypeptides. Such modifications include any chemical modification and comprise single or multiple substitutions, deletions and/or additions of any molecules associated with the protein or peptide, such as carbohydrates, lipids and/or proteins or peptides. The term "derivative" also extends to all functional chemical equivalents of said proteins and peptides.

A variant of a nucleic acid or an amino acid sequence may have a functional property of the nucleic acid or amino acid sequence from which it has been derived. Such functional properties may comprise for example the interaction with receptors or ligands, interaction with antibodies, the interaction with other peptides or proteins, the selective binding of nucleic acids and an enzymatic activity.

In certain embodiments, a non-naturally occurring peptide is a synthetic peptide or an isolated peptide. In certain embodiments, the non-naturally occurring peptide is produced by recombinant DNA technology.

Methods for isolating and/or producing polypeptides and protein are known, and are as described generally in Sambrook, J, Fritsch, E. F. and Maniatis, T. Molecular Cloning: A Laboratory Manual 2nd. ed. Cold Spring Harbor Laboratory Press, New York. (1989), herein incorporated by reference, and Ausubel et al., Current Protocols in Molecular Biology (2011), John Wiley & Sons, Inc., herein incorporated by reference.

Certain embodiments of the present disclosure provide an isolated nucleic acid comprising a nucleotide sequence encoding a polypeptide as described herein. Certain embodiments of the present disclosure provide an isolated nucleic acid comprising a nucleotide sequence encoding a polypeptide comprising one or more or amino acid sequences SEQ ID NOs.5 to 24, or a variant or a fragment thereof.

Confirmation that an antibody binds to a desired epitope may be determined by a known method.

In certain embodiments, the antibody (and/or an antigen binding fragment thereof) is produced by raising the antibody against a chemokine receptor CCX-CKR antigen. In certain embodiments, the antibody (and/or an antigen binding fragment thereof) is produced by raising the antibody against a chemokine receptor CCX-CKR and/or an antigenic fragment thereof. In certain embodiments, the antibody (and/or an antigen binding fragment thereof) is an antibody raised against an animal or human chemokine receptor CCX-CKR. In certain embodiments, the antibody (and/or an antigen binding fragment thereof) is raised against a full length receptor, a variant of a receptor, a fragment of a receptor, a soluble form of the receptor or the receptor expressed on the surface of a cell.

In certain embodiments, the antibody is raised against a chemokine receptor CCX-CKR and/or an antigenic fragment thereof. In certain embodiments, the antibody is raised against an amino terminal region of a chemokine receptor CCX-CKR. In certain embodiments, the antibody is raised against all or part of an extracellular region of a chemokine receptor CCX-CKR. In certain embodiments, the antibody is raised against an amino terminal extracellular region of a chemokine receptor CCX-CKR. In certain embodiments, the antibody is raised against a polypeptide comprising all or part of an extracellular region of a chemokine receptor CCX-CKR and/or a variant thereof. In certain embodiments, the antibody is raised against a polypeptide comprising all or part of an amino terminal region of a chemokine receptor CCX-CKR and/or a variant thereof.

In certain embodiments, the antibody is raised against one or more amino acids (epitopes) located in one or more of the following regions of the human chemokine receptor CCX-CKR: amino acids 1 to 42, amino acids 109 to 113, amino acids 176 to 201, and amino acids 262 to 289; or an equivalent region of the receptor in another species. In certain embodiments, the antibody is raised against a polypeptide comprising one or more amino acids (epitopes) located in one or more of the following regions of the human chemokine receptor CCX-CKR: amino acids 1 to 42, amino acids 109 to 113, amino acids 176 to 201, and amino acids 262 to 289; or an equivalent region of the receptor in another species.

In certain embodiments, the antibody is raised against one or more amino acids (epitopes) located in a region comprising amino acids 1 to 42 of a chemokine receptor CCX-CKR or a variant thereof.

In certain embodiments, the antibody is raised against one or more amino acids (epitopes) located in the following polypeptide sequence: CCX-CKR: MALEQNQST-DYYYEENEMNGTYDYSQYELICIKEDVREFAKV (SEQ ID NO. 5) or a variant thereof.

In certain embodiments, the antibody is raised against or more amino acids (epitopes) located in the following polypeptide sequences: MALEQNQSTDYYYEENEMNG (SEQ ID NO. 6); TYDYSQYELICIKEDVREFAK (SEQ ID NO. 7); MALELNQSAEYY (SEQ ID NO. 13); NYTH-DYSQYEVI (SEQ ID NO. 14). MALEQNQSTDYY (SEQ ID NO.19), NGTYDYSQYE LI (SEQ ID NO.20) or a variant of one of the aforementioned sequences.

In certain embodiments, the antibody is raised against or more amino acids (epitopes) located in a region comprising amino acids 100 to 111 of a chemokine receptor CCX-CKR or a variant thereof. In certain embodiments, the antibody is raised against or more amino acids (epitopes) located in the following polypeptide sequences: NAVHGWILGKMM (SEQ ID NO. 15), NAVHGWVLGKIM (SEQ ID NO. 21) or a variant thereof.

In certain embodiments, the antibody is raised against or more amino acids (epitopes) located in a region comprising amino acids 109 to 113 of a chemokine receptor CCX-CKR or a variant thereof. In certain embodiments, the antibody is raised against or more amino acids (epitopes) located in following polypeptide sequence: KIMCK (SEQ ID NO. 8) or a variant thereof.

In certain embodiments, the antibody is raised against or more amino acids (epitopes) located in a region comprising amino acids 176 to 201 of a chemokine receptor CCX-CKR or a variant thereof. In certain embodiments, the antibody is raised against or more amino acids (epitopes) located in a region comprising amino acids 180 to 191 of a chemokine receptor CCX-CKR or variant thereof. In certain embodiments, the antibody is raised against or more amino acids (epitopes) located in a region comprising amino acids 186 to 197 of a chemokine receptor CCX-CKR or a variant thereof.

In certain embodiments, the antibody is raised against or more amino acids (epitopes) located in following polypeptide sequence: YTVNDNARCIPIFPRYLGTSMKALIQ (SEQ ID NO. 9) or a variant thereof. In certain embodiments, the antibody is raised against or more amino acids (epitopes) in the following polypeptide sequences: QNARCTPIFPHH (SEQ ID NO. 16), DNARCIPIFPRY (SEQ ID NO.22) or a variant thereof. In certain embodiments, the antibody is raised against or more amino acids (epitopes) in the following polypeptide sequences: PIFPHHLGTSLK (SEQ ID NO. 17), PIFPRYLGTSMK (SEQ ID NO. 23) or a variant thereof.

In certain embodiments, the antibody is raised against or more amino acids (epitopes) located in a region comprising amino acids 262 to 289 of a chemokine receptor CCX-CKR or a variant thereof. In certain embodiments, the antibody is raised against or more amino acids (epitopes) located in a region comprising amino acids 276 to 287 of a chemokine receptor CCX-CKR or a variant thereof.

In certain embodiments, the antibody is raised against or more amino acids (epitopes) in the following polypeptide sequence: CRAIDIIYSLITSCNMSKRMDIAIQVTE (SEQ ID NO. 10) or a variant thereof. In certain embodiments, the antibody is raised against or more amino acids (epitopes) in the following polypeptide sequences: DMSKRMDVAIQV (SEQ ID NO. 18), NMSKRMDIAIQV (SEQ ID NO.24) or a variant thereof.

In certain embodiments, the antibody is raised against or more amino acids (epitopes) located in one or more of SEQ ID NOs. 5 to 24, and/or a variant or fragment thereof. In certain embodiments, the antibody is raised against a polypeptide comprising an amino acid sequences selected from one or more of SEQ ID NOs.5 to 24, or a variant or fragment of any one or more of these sequences. In certain embodiments, the antibody is raised an isolated or synthetic polypeptide consisting of an amino acid sequence selected from one or more of SEQ ID NOs.5 to 24, or a variant or fragment thereof.

In certain embodiments, an antibody and/or antigen binding fragment thereof has a Kd for binding of greater than $10^{-6}$M. In further embodiments, a Kd for binding is equal to or greater than $10^{-7}$M, $10^{-8}$M, $10^{-9}$M or $10^{-10}$M. In further embodiments, a Kd for binding is at least $10^{-7}$M, $10^{-8}$M, $10^{-9}$M or $10^{-10}$M. In certain embodiments, the Kd is in the range from $10^{-8}$M to $10^{-12}$M.

Certain embodiments of the present disclosure provide an antibody to a chemokine receptor CCX-CKR and/or an antigen binding fragment thereof as described herein. Certain embodiments of the present disclosure provide use of an antibody and/or an antigen binding fragment thereof in the preparation of a medicament.

Certain embodiments of the present disclosure provide an antibody to chemokine receptor CCX-CKR and/or an antigen binding fragment thereof, wherein the antibody and/or the antigen binding fragment thereof inhibits metastasis of a cancer.

Certain embodiments of the present disclosure provide an antibody to chemokine receptor CCX-CKR and/or an antigen binding fragment thereof, wherein the antibody and/or the antigen binding fragment thereof inhibits a metastatic cancer. Cancers are as described herein.

Certain embodiments of the present disclosure provide an antibody that binds to an extracellular region of a chemokine receptor CCX-CKR and/or an antigen binding fragment of the antibody.

Certain embodiments of the present disclosure provide an antibody raised to an epitope on an extracellular region of a chemokine receptor CCX-CKR and/or an antigen binding fragment of the antibody.

Certain embodiments of the present disclosure provide an antibody that binds to an epitope located in one or more of the following regions of a human chemokine receptor CCX-CKR: amino acids 1 to 42, amino acids 109 to 113, amino acids 176 to 201, and amino acids 262 to 289; or an equivalent region of the receptor in another species.

Certain embodiments of the present disclosure provide an antibody raised against a polypeptide comprising all or part of one or more of the following polypeptide sequences: SEQ ID NOs. 5 to 24, and/or a variant thereof.

Certain embodiments of the present disclosure provide an antibody to a chemokine receptor CCX-CKR and/or an antigen binding fragment thereof, wherein the antibody and/or the antigen binding fragment thereof inhibits metastasis of a cancerous cell.

Examples of metastatic cancers are as described herein. Examples of metastasis of cancers are as described herein. In certain embodiments, the metastatic cancer is a metastatic melanoma, a breast cancer, a prostate cancer, an ovarian cancer, or a colorectal cancer.

In certain embodiments, the metastasis of a cancer is metastasis of a melanoma, a breast cancer, a prostate cancer, an ovarian cancer, or a colorectal cancer In certain embodiments, the antibody and/or the antigen binding fragment thereof as described herein binds to region of a CCX-CKR, as described herein.

In certain embodiments, the antibody and/or the antigen binding fragment thereof binds to an extracellular region of a CCX-CKR, as described herein. In certain embodiments, the antibody and/or the antigen binding fragment thereof binds to an amino terminal region of a CCX-CKR, as described herein. In certain embodiments, the antibody and/or antigen binding fragment thereof binds to an amino terminal extracellular region of a CCX-CKR, as described herein. In certain embodiments, the antibody binds to a region comprising one or more amino acids located in a region from amino acids 1 to 12, 1 to 41 or 42, 1 to 20, 19 to 30, 21 to 41, 100 to 111, 109 to 113, 176 to 201, 180 to 191, 186 to 197, 262 to 289, or 276 to 287 of a CCX-CKR receptor, as described herein.

In certain embodiments, the antibody and/or the antigen binding fragment thereof binds to one or more amino acids or an epitope in one or more of polypeptide sequences SEQ ID NOs 5 to 24.

In certain embodiments, the antibody is raised against a chemokine receptor CCX-CKR and/or an antigenic fragment thereof, as described herein.

In certain embodiments, the antibody is raised against all or part of an extracellular region of a chemokine receptor CCX-CKR or a variant thereof, as described herein. In certain embodiments, the antibody and/or the antigen binding fragment thereof is raised against an amino terminal region of a chemokine receptor CCX-CKR or a variant thereof, as described herein. In certain embodiments, the antibody is raised against an amino terminal extracellular region of a chemokine receptor CCX-CKR or a variant thereof, as described herein.

In certain embodiments, the antibody is raised against a region comprising one or more amino acids located in a region from amino acids 1 to 12, 1 to 41 or 42, 1 to 20, 19 to 30, 21 to 41, 100 to 111, 109 to 113, 176 to 201, 180 to 191, 186 to 197, 262 to 289, or 276 to 287 of a chemokine receptor CCX-CKR or variant thereof, as described herein.

In certain embodiments, the antibody is raised against a region comprising one or more amino acids located in a region from amino acids 1 to 12, 1 to 41 or 42, 1 to 20, 19 to 30, 21 to 41, 100 to 111, 109 to 113, 176 to 201, 180 to 191, 186 to 197, 262 to 289, or 276 to 287 of a human chemokine receptor CCX-CKR, or an equivalent region of the receptor in another species, or a variant of any of the aforementioned.

In certain embodiments, the antibody is raised against a polypeptide comprising all or part of one or more of polypeptide sequences SEQ ID NOs 5 to 24, and/or a variant of any of the aforementioned sequences.

In certain embodiments, the antibody is a polyclonal antibody and/or an antigen binding fragment thereof, as described herein. In certain embodiments, the antibody is a monoclonal antibody and/or an antigen binding fragment thereof, as described herein. In certain embodiments, the antibody is a human antibody or a humanized antibody.

In certain embodiments, the antibody and/or the antigen binding fragment thereof is neutralising for a chemokine receptor CCX-CKR. In certain embodiments, the antibody and/or antigen binding fragment thereof is an antagonist of a chemokine receptor CCX-CKR. In certain embodiments, the antibody and/or the antigen binding fragment thereof reduces binding of a ligand to a chemokine receptor CCX-CKR, as described herein. In certain embodiments, the antibody and/or the antigen binding fragment thereof promotes internalisation of a chemokine receptor CCX-CKR.

In certain embodiments, the antibody has an isotype as described herein. In certain embodiments, the antibody has an isotype selected from the group consisting of IgG1, IgG2a, IgG2b, IgG3, IgM and IgA, as described herein.

In certain embodiments, the antibody is a polyclonal antibody and/or antigen binding fragment thereof, as described herein. In certain embodiments, the antibody is a monoclonal antibody and/or an antigen binding fragment thereof, as described herein. In certain embodiments, the antibody is a human antibody or a humanized antibody, as described herein.

Certain embodiments of the present disclosure provide a method of producing an antibody and/or an antigen binding fragment thereof as described herein. Methods for producing antibodies and antigen binding fragments are known.

Certain embodiments of the present disclosure provide a method of producing an antibody, the method comprising raising the antibody to a region of a chemokine receptor CCX-CKR and/or a polypeptide as described herein.

Certain embodiments provide one or more cells expressing an antibody (or an antigen-binding fragment thereof) as described herein. In certain embodiments, the one or more cells comprise one or more isolated cells. Examples of cell include prokaryotic cells, and eukaryotic cells such as insect cells and mammalian cells. The antibody or antigen binding fragment may be expressed recombinantly.

In certain embodiments, the isolated cell is a hybridoma cell. Certain embodiments provide a hybridoma cell expressing an antibody as described herein. Methods for producing hybridoma cells are known.

For example, a typical protocol is as follows: Animals (e.g. mice) are first exposed to the selected antigen. Usually this is done by a series of injections of the antigen, over the course of several weeks. Once splenocytes are isolated from the mammal's spleen, the B cells may be fused with immortalised myeloma cells. The myeloma cells are generally selected to ensure they are not secreting antibody themselves and that they lack the hypoxanthine-guanine phosphoribosyltransferase (HGPRT) gene, making them sensitive to HAT medium. The fusion may be accomplished, for example, using polyethylene glycol or Sendai virus.

Fused cells are incubated in HAT medium for roughly 10 to 14 days. Aminopterin blocks the pathway that allows for nucleotide synthesis and unfused myeloma cells die, as they cannot produce nucleotides by the de novo or salvage pathways because they lack HGPRT. Removal of the unfused myeloma cells is necessary because they have the potential to outgrow other cells, especially weakly established hybridomas. Unfused B cells die as they have a short life span. In this way, only the B cell-myeloma hybrids survive, since the HGPRT gene coming from the B cells is functional. These cells produce antibodies and are immortal. The incubated medium is then diluted into multi-well plates to such an extent that each well contains only one cell. Since the antibodies in a well are produced by the same B cell, they will be directed towards the same epitope, and are thus monoclonal antibodies.

The next stage is a rapid primary screening process, which identifies and selects only those hybridomas that produce antibodies of appropriate specificity. The hybridoma culture supernatant, secondary enzyme labeled conjugate, and chromogenic or fluorescent substrate, are then incubated, and the formation of a colored product indicates a positive hybridoma. Alternatively, immunocytochemical screening or flow cytometry can also be used.

The B cell that produces the desired antibodies can be cloned to produce many identical daughter clones. Supplemental media containing interleukin-6 are essential for this step. Once a hybridoma colony is established, it will continually grow in culture medium like RPMI-1640 (with antibiotics and fetal bovine serum) and produce antibodies.

Multiwell plates are used initially to grow the hybridomas, and after selection, are changed to larger tissue culture flasks. This maintains the well-being of the hybridomas and provides enough cells for cryopreservation and supernatant for subsequent investigations. The culture supernatant can yield 1 to 60 µg/ml of monoclonal antibody, which is maintained at −20° C. or lower until required.

By using culture supernatant or a purified immunoglobulin preparation, further analysis of a potential monoclonal antibody producing hybridoma can be made in terms of reactivity, specificity, and cross-reactivity.

Certain embodiments provide an isolated nucleic acid comprising a nucleotide sequence encoding an antibody and/or an antigen binding part thereof, as described herein. Certain embodiments provide an expression vector comprising the nucleic acid. Certain embodiments provide a cell including the nucleic acid and/or the expression vector.

Certain embodiments of the present disclosure provide a method of inhibiting metastasis of a cancerous cell, the method comprising exposing the cell to an effective amount of an inhibitor of a chemokine receptor CCX-CKR.

The term "exposing", and related terms such as "expose" and "exposure", refers to directly and/or indirectly contacting and/or treating a species (for example a cancerous cell) with an agent that directly and/or indirectly inhibits a CCX-CKR.

For cells in vivo, an inhibitor may be administered to a subject to expose cells to an inhibitor, or an agent may be administered to a subject that results in the production of an inhibitor in the subject, thereby exposing cells in vivo to an inhibitor. In another example, one or more cells may be removed from a subject and contacted directly or indirectly with an inhibitor, and cells then introduced back into the same or another subject to effect exposure to an inhibitor. Examples of administration routes are as described herein. In certain embodiments, the cell is present ex vivo. For example, a cancerous cell may exposed to an inhibitor ex vivo, and subsequently be introduced into a subject.

Certain embodiments of the present disclosure provide a method of inhibiting metastasis of a cancerous cell in vivo or ex vivo, the method comprising exposing the cell to an inhibitor of a chemokine receptor CCX-CKR. Inhibitors of a chemokine receptor CCX-CKR are described herein. In certain embodiments, the inhibitor comprises an antibody and/or an antigen binding fragment thereof as described herein.

Certain embodiments of the present disclosure provide a method of inhibiting metastasis of a cancerous cell in vivo or ex vivo, the method comprising exposing the cell to an effective amount of an antibody (and/or an antigen binding fragment thereof) to a chemokine receptor CCX-CKR. Antibodies, and antigen binding fragments thereof, are described herein.

The term "effective amount" as used herein refers to that amount of an agent that when exposed to a cell or another species is sufficient to illicit the desired response or outcome. The effective amount will vary depending upon a number of factors, including for example the specific activity of the agent being used and the cancerous cell type.

In certain embodiments, a cancerous cell or a metastatic cancer is exposed to a concentration of an inhibitor of 0.1 nM or greater, 0.5 nM or greater, 1 nM or greater, 5 nM or greater, 10 nM or greater, 50 nM or greater, 100 nM or greater, 500 nM or greater, 1 uM or greater, 5 uM or greater, 10 uM or greater, 100 uM or greater, 500 uM or greater, 1 mM or greater, or 10 mM or greater. Other concentrations are contemplated.

In certain embodiments, a cancerous cell or a metastatic cancer is exposed to an antibody, and/or an antigen binding fragment thereof, at one of the aforementioned concentrations.

In certain embodiments, a cancerous cell or a metastatic cancer is exposed to an inhibitor in an amount ranging from one of the following selected ranges: 1 µg/kg to 100 mg/kg; 1 µg/kg to 10 mg/kg; 1 µg/kg to 1 mg/kg; 1 µg/kg to 100 µg/kg; 1 µg/kg to 10 µg/kg; 10 µg/kg to 100 mg/kg; 10 µg/kg to 10 mg/kg; 10 µg/kg to 1 mg/kg; 10 µg/kg to 100 µg/kg; 100 µg/kg to 100 mg/kg; 100 µg/kg to 10 mg/kg; 100 µg/kg to 1 mg/kg; 1 mg/kg to 10 mg/kg; and 10 mg/kg to 100 mg/kg body weight. Other amounts are contemplated. In certain embodiments, a cancerous cell or a metastatic cancer is exposed to an antibody, and/or an antigen binding fragment thereof, at one of the aforementioned amounts.

Examples of cancerous cells include cancerous cells from cancers as described herein. In certain embodiments, the cancerous cell is a solid cancer cell. In certain embodiments, the cancerous cell is a carcinoma cell. In certain embodiments, the cancerous cell is a sarcoma cell. In certain embodiments, the cancerous cell is a lymphoma cell. In certain embodiments, the cancer cell is a germ cell cancerous cell. In certain embodiments, the cancerous cell is a blastoma cell. In certain embodiments, the cancerous cell is a haematological cancerous cell.

In certain embodiments, the cancerous cell is a melanoma cell, a cancerous breast cell, a cancerous prostate cell, a cancerous ovarian cell, a cancerous lung cell, a cancerous colorectal cell, a cancerous gastric cell, a cancerous pancreatic cell, a cancerous bladder cell, a cancerous oesophageal cell, a cancerous urothelial cell, a cancerous non-small cell lung cell, a cancerous head & neck cell, a cancerous testicular cell, a cancerous uterine cell, a cancerous liver cell, a cancerous renal cell, a cancerous stomach cell, a cancerous brain cell, a malignant myeloma cell, a cancerous CML cell, a cancerous AML cell, or a cell from a lymphoproliferative tumour. Other types of cancers are contemplated.

In certain embodiments, the cancerous cell is a melanoma cell, a breast cancer cell, a prostate cancer cell, an ovarian cancer cell, or a colorectal cancer cell.

Inhibitors of a chemokine receptor CCX-CKR are described herein. In certain embodiments, the inhibitor comprises one or more of a small interfering RNA, an antisense RNA, a ligand for a chemokine receptor CCX-CKR, and an antibody and/or an antigen binding fragment thereof.

In certain embodiments, the inhibitor reduces binding of a ligand to a chemokine receptor CCX-CKR, as described herein. In certain embodiments, the inhibitor promotes internalisation of a chemokine receptor CCX-CKR. In certain embodiments, the inhibitor comprises an antibody and/or an antigen binding fragment thereof as described herein.

Certain embodiments of the present disclosure provide a method of inhibiting growth of a metastatic cancerous cell, the method comprising exposing the cell to an effective amount of inhibitor of a chemokine receptor CCX-CKR, as described herein. Metastatic cells are as described herein.

Certain embodiments of the present disclosure provide a method of inhibiting growth of a metastatic cancerous cell, the method comprising exposing the cell to an effective amount of an antibody and/or an antigen binding fragment thereof, as described herein.

Certain embodiments of the present disclosure provide a method of preventing and/or treating metastatic cancer in a subject, the method comprising administering to the subject a therapeutically effective amount of inhibitor to a chemokine receptor CCX-CKR, as described herein.

Certain embodiments of the present disclosure provide a method of preventing and/or treating metastatic cancer in a subject, the method comprising administering to the subject a therapeutically effective amount of an antibody and/or an antigen binding fragment thereof, as described herein.

Certain embodiments of the present disclosure provide a method of preventing and/or treating metastasis of a cancer in a subject, the method comprising administering to the subject a therapeutically effective amount of an inhibitor to a chemokine receptor CCX-CKR, as described herein.

Certain embodiments of the present disclosure provide a method of preventing and/or treating metastasis of a cancer in a subject, the method comprising administering to the subject a therapeutically effective amount of an antibody and/or an antigen binding fragment thereof, as described herein.

The term "therapeutically effective amount" as used herein refers to that amount of an agent that is sufficient to effect prevention and/or treatment, when administered to a subject. The therapeutically effective amount will vary depending upon a number of factors, including for example the specific activity of the agent being used, the severity of the disease, condition or state in the subject, the age, physical condition, existence of other disease states, and nutritional status of the subject.

In certain embodiments, the inhibitor is administered to the subject to produce a concentration of an inhibitor of 0.1 nM or greater, 0.5 nM or greater, 1 nM or greater, 5 nM or greater, 10 nM or greater, 50 nM or greater, 100 nM or greater, 500 nM or greater, 1 uM or greater, 5 uM or greater, 10 uM or greater, 100 uM or greater, 500 uM or greater, 1 mM or greater, or 10 mM or greater. In certain embodiments, an antibody and/or an antigen binding fragment thereof is administered to the subject to produce a concentration in one of the aforementioned ranges.

In certain embodiments, the inhibitor is administered to the subject in an amount ranging from one of the following selected ranges: 1 µg/kg to 100 mg/kg; 1 µg/kg to 10 mg/kg; 1 µg/kg to 1 mg/kg; 1 µg/kg to 100 µg/kg; 1 µg/kg to 10 µg/kg; 10 µg/kg to 100 mg/kg; 10 µg/kg to 10 mg/kg; 10 µg/kg to 1 mg/kg; 10 µg/kg to 100 µg/kg; 100 µg/kg to 100 mg/kg; 100 µg/kg to 10 mg/kg; 100 □g/kg to 1 mg/kg; 1 mg/kg to 10 mg/kg; and 10 mg/kg to 100 mg/kg body weight. In certain embodiments, an antibody and/or an antigen binding fragment thereof is administered to the subject to produce in one of the aforementioned ranges. For example, a therapeutic antibody may be administered at a concentration of 0.5, 1, 2, 3, 4, 5, 10, 15 or 20 mg/kg body weight. Other amounts are contemplated. The dose and frequency of administration may be determined by one of skill in the art.

The inhibitor may be administered to the subject in a suitable form. In this regard, the terms "administering" or "providing" includes administering the inhibitor, or administering a prodrug of the inhibitor, or a derivative of the inhibitor that will form a therapeutically effective amount of the inhibitor within the body of the subject. The terms include routes of administration that are systemic (e.g., via injection such as intravenous injection, orally in a tablet, pill, capsule, or other dosage form useful for systemic administration of pharmaceuticals), and topical (e.g., creams, solutions, and the like, including solutions such as mouthwashes, for topical oral administration).

In certain embodiments, the inhibitor is administered orally. In certain embodiments, the inhibitor is administered intravenously. In certain embodiments, the inhibitor is administered via injection such as intravenous injection. In certain embodiments, the inhibitor is administered by nebulized administration, by aerosolized administration or by being instilled into the lung.

The inhibitors may be administered alone or may be delivered in a mixture with other therapeutic agents and/or agents that enhance, stabilise or maintain the activity of the inhibitor. In certain embodiments, an administration vehicle (e.g., pill, tablet, implant, injectable solution, etc.) would contain both the inhibitor(s) and additional agent(s).

The methods may also include combination therapy. In this regard, the subject is treated or given another drug or treatment modality in conjunction with the inhibitor as described herein. This combination therapy can be sequential therapy where the subject is treated first with one and then the other, or the two or more treatment modalities are given simultaneously.

"Co-administering" or "co-administration" refers to the administration of two or more therapeutic agents together at one time. The two or more therapeutic agents can be co-formulated into a single dosage form or "combined dosage unit", or formulated separately and subsequently combined into a combined dosage unit, typically for intravenous administration or oral administration.

When administered to a subject the therapeutically effective dosage may vary depending upon the particular inhibitor utilized, the mode of administration, the condition, and severity thereof, as well as the various physical factors related to the subject being treated. As discussed herein, suitable daily doses range from 1 µg/kg to 100 mg/kg. The daily dosages are expected to vary with route of administration, and the nature of the inhibitor administered. In certain embodiments the methods comprise administering to the subject escalating doses of inhibitor and/or repeated doses. In certain embodiments, the inhibitor is administered orally. In certain embodiments, the inhibitor is administered via injection, such as intravenous injection. In certain embodiments, the inhibitor is administered parenterally. In certain embodiments, the inhibitor is administered by direct introduction to the lungs, such as by aerosol administration, by nebulized administration, and by being instilled into the lung. In certain embodiments, the inhibitor is administered by implant. In certain embodiments, the certain embodiments, the inhibitor is administered by subcutaneous injection, intraarticularly, rectally, intranasally, intraocularly, vaginally, or transdermally.

"Intravenous administration" is the administration of substances directly into a vein.

"Oral administration" is a route of administration where a substance is taken through the mouth, and includes buccal, sublabial and sublingual administration, as well as enteral administration and that through the respiratory tract, unless made through e.g. tubing so the medication is not in direct contact with any of the oral mucosa. Typical form for the oral administration of therapeutic agents includes the use of tablets or capsules.

In certain embodiments, the inhibitor is administered as an immediate release formulation. The term "immediate release formulation" is a formulation which is designed to quickly release a therapeutic agent in the body over a shortened period of time.

In certain embodiments, the inhibitor is administered as a sustained release formulation. The term "sustained release formulation" is a formulation which is designed to slowly release a therapeutic agent in the body over an extended period of time.

In certain embodiments, the inhibitor may be used in a pharmaceutical composition. In certain embodiments, the inhibitor may be used in a pharmaceutical composition for use in the methods of the present disclosure as described herein. In certain embodiments, the inhibitor may be used in a medicament or in the preparation of a medicament.

Certain embodiments of the present disclosure provide a pharmaceutical composition comprising an inhibitor of a chemokine receptor CCX-CKR as described herein. In certain embodiments, the pharmaceutical composition comprises an antibody and/or an antigen binding part thereof as described herein.

Certain embodiments of the present disclosure provide a pharmaceutical composition when used to prevent and/or treat metastatic cancer, the pharmaceutical composition comprising a therapeutically effective amount of an inhibitor of a chemokine receptor CCX-CKR.

In certain embodiments, the pharmaceutical composition further comprises one or more of a pharmaceutically acceptable carrier, excipient, vehicle and additive.

Certain embodiments of the present disclosure provide an inhibitor of a chemokine receptor CCX-CKR for use in preventing and/or treating metastatic cancer. Inhibitors are as described herein.

Certain embodiments of the present disclosure provides use of an inhibitor of a chemokine receptor CCX-CKR in the preparation of a medicament for preventing and/or treating metastatic cancer. Inhibitors are as described herein.

In certain embodiments, the inhibitor is present in a medicament so as to produce a concentration of an inhibitor in the subject of 0.1 nM or greater, 0.5 nM or greater, 1 nM or greater, 5 nM or greater, 10 nM or greater, 50 nM or greater, 100 nM or greater, 500 nM or greater, 1 uM or greater, 5 uM or greater, 10 uM or greater, 100 uM or greater, 500 uM or greater, 1 mM or greater, or 10 mM or greater. Other concentrations are contemplated. In certain embodiments, a therapeutic antibody and/or an antigen binding fragment thereof is present in a medicament in one of the aforementioned amounts.

In certain embodiments, the inhibitor in a medicament is present so as to provide an amount of inhibitor for administration to the subject in an amount ranging from one of the following selected ranges: 1 µg/kg to 100 mg/kg; 1 µg/kg to 10 mg/kg; 1 µg/kg to 1 mg/kg; 1 µg/kg to 100 µg/kg; 1 µg/kg to 10 µg/kg; 10 µg/kg to 100 mg/kg; 10 µg/kg to 10 mg/kg; 10 µg/kg to 1 mg/kg; 10 µg/kg to 100 µg/kg; 100 µg/kg to 100 mg/kg; 100 µg/kg to 10 mg/kg; 100 µg/kg to 1 mg/kg; 1 mg/kg to 10 mg/kg; and 10 mg/kg to 100 mg/kg body weight. Other amounts are contemplated. In certain embodiments, a therapeutic antibody and/or an antigen binding fragment thereof is present in a medicament in one of the aforementioned amounts.

In certain embodiments, the medicament is suitable for delivery to the subject by one or more of intravenous administration, intratracheal administration, by nebulized administration, by aerosolized administration, by instillation into the lung, by oral administration, by parenteral administration, by implant, by subcutaneous injection, intraarticularly, rectally, intranasally, intraocularly, vaginally, or transdermally.

In certain embodiments, the inhibitor is provided in a pharmaceutically acceptable carrier suitable for administering the pharmaceutical composition to a subject. The carriers may be chosen based on the route of administration as described herein, the location of the target issue, the inhibitor being delivered, the time course of delivery of the drug, etc. The term "pharmaceutically acceptable carrier" refers to a substantially inert solid, semi-solid or liquid filler, diluent, encapsulating material or formulation auxiliary of any type. An example of a pharmaceutically acceptable carrier is physiological saline. Other physiologically acceptable carriers and their formulations are known in the art. Some examples of materials which can serve as pharmaceutically acceptable carriers include, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as TWEEN 80; buffering agents such as magnesium hydroxide and aluminium hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as colouring agents, releasing agents, coating agents, sweetening, flavouring and perfuming agents, preservatives and antioxidants can also be present.

In certain embodiments, the inhibitor may be administered or present in a pharmaceutical composition as a pharmaceutically acceptable salt. The term "pharmaceutically acceptable salt" refers to acid addition salts or metal complexes which are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acids such as hydrochloric acid, hydrobromic acid, sulfuric acid phosphoric acid, or the like. Metal complexes include zinc, iron, and the like.

In certain embodiments, the pharmaceutical compositions or medicament comprises other therapeutic agents and/or agents that enhance, stabilise or maintain the activity of the active.

Oral formulations containing the inhibitors as described herein may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including magnesium stearate, stearic acid, talc, sodium lauryl sulfate, microcrystalline cellulose, carboxymethylcellulose calcium, polyvinylpyrrolidone, gelatin, alginic acid, *acacia* gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidol silicon dioxide, phosphates, sodium dodecylsulfate, magnesium aluminium silicate, and triethanolamine. Oral formulations may utilize standard delay or time-release formulations to alter the absorption of the peptides. The oral formulation may also consist of administering the active ingredient in water or a fruit juice, containing appropriate solubilizers or emulsifiers as needed.

In certain embodiments, it may be desirable to administer the inhibitor directly to the airways in the form of an aerosol. Formulations for the administration of aerosol forms are known.

In certain embodiments, the inhibitor may also be administered parenterally (such as directly into the joint space) or intraperitoneally. For example, solutions or suspensions of these compounds in a non-ionised form or as a pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations typically contain a preservative to prevent the growth of microorganisms.

In certain embodiments, the inhibitor may also be administered by injection. Pharmaceutical forms suitable for injectable use include sterile aqueous solutions or dispersions and sterile powders for the extemporaneous preparation of sterile injectable solutions or dispersions. The carrier can be a solvent or dispersion medium containing, for example, water, ethanol, polyol (e.g., glycerol, propylene glycol and liquid polyethylene glycol), suitable mixtures thereof, and vegetable oils.

In certain embodiments, the inhibitor may also be administered intravenously. Compositions containing the inhibitor described herein suitable for intravenous administration may be formulated by a skilled person.

In certain embodiments, the inhibitor may also be administered transdermally. Transdermal administrations are understood to include all administrations across the surface of the body and the inner linings of bodily passages including epithelial and mucosal tissues. Such administrations may be carried out using the inhibitor as described herein, or pharmaceutically acceptable salts thereof, in lotions, creams, foams, patches, suspensions, solutions, and suppositories (rectal and vaginal).

Transdermal administration may also be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient.

In certain embodiments, the inhibitor may also be administered by way of a suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

Additional numerous various excipients, dosage forms, dispersing agents and the like that are suitable for use in connection with the administration of the inhibitor and/or the formulation into medicaments or pharmaceutical compositions.

Formulations are known and described in, for example, Remington's Pharmaceutical Sciences, 17th ed., Mack Publishing Company, Easton, Pa., 1985, which is incorporated herein by reference in its entirety.

For the administration of an antibody and/or an antigen binding fragment thereof, these may be incorporated into a pharmaceutical composition, generally along with a pharmaceutically acceptable carrier, suitable for administration to a subject in vivo.

Certain embodiments of the present disclosure provide a pharmaceutical composition comprising an antibody and/or antigen binding part thereof, as described herein. Methods for preparing, formulating and administering pharmaceutical compositions comprising an antibody are known, and include for example "Handbook of Therapeutic Antibodies" ed. S. Dubel (2007) Wiley-VCH. In certain embodiments, the pharmaceutical composition comprises a pharmaceutically acceptable carrier, as described herein.

Certain embodiments of the present disclosure provide an antibody and/or antigen binding fragment thereof for use in a medicament, as described herein.

Certain embodiments of the present disclosure provide an antibody and/or an antigen binding fragment thereof for use in preventing and/or treating metastatic cancer, as described herein.

Certain embodiments of the present disclosure provide a method of detecting a chemokine receptor CCX-CKR.

In certain embodiments, an antibody and/or an antigen binding fragment thereof as described herein is used to detect a chemokine receptor CCX-CKR. Various methods are known for using antibodies to detect receptors, and are as described generally in Sambrook, J, Fritsch, E. F. and Maniatis, T. Molecular Cloning: A Laboratory Manual 2nd. ed. Cold Spring Harbor Laboratory Press, New York. (1989), herein incorporated by reference.

In certain embodiments, the antibody and/or antigen-binding fragment thereof as described herein may be used as a diagnostic agent to detect a chemokine receptor CCX-CKR in vitro, ex vivo and/or in vivo. For example, antibodies may be used in a conventional immunoassay, including an ELISA, an RIA, FACS, tissue immunohistochemistry, Western blot or immunoprecipitation.

Certain embodiments of the present disclosure provide a method of detecting a cancerous cell expressing or overexpressing a chemokine receptor CCX-CKR. Certain embodiments of the present disclosure provide a method of detecting a cancer, including a metastatic cancer.

In certain embodiments, an antibody and/or an antigen binding fragment thereof as described herein is used to detect a cancerous cell, a cancer or a metastatic cancer. In certain embodiments, the cancerous cell is a metastatic cancerous cell. In certain embodiments, an antibody and/or an antigen binding fragment thereof is used to detect a cancerous cell, a metastatic cancerous cell, a cancer or a metastatic cancer expressing or over-expressing chemokine receptor CCX-CKR.

In certain embodiments, for the use of the detection of a chemokine receptor CCX-CKR, or detection of a cell or cancer expressing or overexpressing CCX-CKR, the antibody and/or antigen-binding portion may labelled with a detectable moiety and thereby the receptor or cell detected directly.

Alternatively, a primary antibody to a chemokine receptor CCX-CKR may be unlabeled and a secondary antibody or other molecule that binds to the chemokine receptor CCX-CKR antibody can be utilised. For example, the antibody may be used in immunohistochemical analysis of tissues or cells. The binding of antibody may be detected with a secondary antibody, for example such as a biotinylated IgG that recognises the primary antibody, and incubation with Streptavidin CY3/FITC used to detect the binding of the antibody to the receptor.

Examples of detectable moieties include radioisotopes, such as 3H, 14C, 32P, 35S, or 131I; fluorescent or chemi-luminescent compounds, such as fluorescein isothiocyanate, rhodamine, or luciferin; or an enzyme, such as alkaline phosphatase, beta-galactosidase or horseradish peroxidase. Methods for conjugating an antibody to a detectable moiety are known.

Certain embodiments of the present disclosure provide a method of detecting a cancerous cell in a subject. Certain embodiments of the present disclosure provide a method of detecting a metastatic cancerous cell in a subject. Certain embodiments of the present disclosure provide a method of detecting a cancer in a subject. Certain embodiments of the present disclosure provide a method of detecting a metastatic cancer in a subject.

In certain embodiments, the method of detecting comprises using an antibody and/or an antigen binding fragment thereof, as described herein.

In certain embodiments, a sample comprising one or more cells is obtained from a subject, and the present of one or more cancerous cells is detected. In certain embodiments, a sample comprising one or more cells is obtained from a subject, and the present of one or more cancerous cells is detected. Methods for detecting a CCX-CKR, or a cell expressing a CCX-CKR, are described herein In certain embodiments, a cancerous cell, a cancer or a metastatic cancer is detected in situ. In certain embodiments, an antibody and/or an antigen binding fragment thereof as described herein are used for detecting a cancerous cell in vivo, such as in vivo imaging. In certain embodiments, the antibody and/or antigen-binding fragment thereof is labelled with a detectable moiety, such as a radio-opaque agent or radioisotope administered to a subject, and the presence and location of the labelled antibody etc in the host is assayed. Such imaging techniques are useful in the staging and treatment of malignancies. The antibody and/or an antigen binding fragment thereof may be labelled with any moiety that is detectable in a host, whether by nuclear magnetic resonance, radiology, or other detection means known for in vivo imaging are utilised.

Certain embodiments of the present disclosure provide a method of detecting a cancerous cell in a subject, the method comprising:
  administering to the subject an effective amount of an antibody and/or an antigen binding fragment thereof, as described herein; and
  detecting the cancerous cell.

Examples of cancerous cells are as described herein.

Examples of subjects in which a cancerous cell may be detected are as described herein. Subjects are as described herein. In certain embodiments, the subject is human.

Certain embodiments of the present disclosure provide a method of detecting a cancer in a subject, the method comprising:
  administering to the subject an effective amount of an antibody and/or an antigen binding fragment thereof, as described herein; and
  detecting the cancerous.

In certain embodiments, the cancer is a metastatic cancer. Examples of cancers and metastatic cancers are as described herein.

Certain embodiments of the present disclosure provide a method of identifying an agent capable of inhibiting metastasis of a cancer.

Certain embodiments of the present disclosure provide a method of identifying an agent capable of inhibiting metastasis of a cancer, the method comprising:
  identifying a test agent that modulates chemokine receptor CCX-CKR activity;
  determining the ability of the test agent to inhibit metastasis of a cancer; and identifying the test agent as an agent capable of inhibiting metastasis of a cancer.

Certain embodiments of the present disclosure provide an agent identified using the method.

Examples of cancers are as described herein.

Examples of test agents include a drug, a small molecule, a protein, a polypeptide, a lipid, a carbohydrate, a nucleic acid, an oligonucleotide, a ribozyme, a biologic, an aptamer, a cofactor, a ligand, a ligand mimetic, a receptor, an enzyme, a kinase, a phosphatase, a cytokine, a growth factor, a metal ion, a chelate, an antisense nucleic acid, an antisense RNA, a microRNA, a siRNA, an antibody or antigen binding part thereof, an antagonist, an inhibitor, or a suppressor.

In certain embodiments, the test agent comprises an antibody and/or an antigen binding fragment thereof, a small interfering RNA, an antisense RNA, or a ligand for chemokine receptor CCX-CKR.

Methods for determining the ability of a test agent to modulate receptor activity are known. For example, the ability of a test agent to modulate chemokine receptor CCX-CKR activity may include the ability of the test agent to modulate ligand binding to the receptor and/or the ability of the test agent to modulate signalling of the receptor. In this regard, the ability of the test agent to modulate signalling by one or more G proteins may be determined.

Methods for determining the ability of the test agent to inhibit metastasis are known. For example, the ability of the test agent to inhibit metastasis may be determined in a suitable animal model as described herein. Identification of the test agent as an agent capable of inhibiting metastasis may then be accomplished.

Certain embodiments of the present disclosure provide a method of identifying an agent capable of inhibiting cancerous cell metastasis, the method comprising:
  identifying a test agent that inhibits a chemokine receptor CCX-CKR;
  determining the ability of the test agent to inhibit cancerous cell metastasis; and identifying the test agent as an agent capable of inhibiting cancerous cell metastasis.

Certain embodiments of the present disclosure provide an agent identified using the method.

Certain embodiments provide a method of identifying an antibody and/or antigen binding fragment thereof capable of inhibiting cancerous cell metastasis.

Certain embodiments provide a method of identifying an antibody and/or antigen binding fragment thereof capable of inhibiting cancerous cell metastasis, the method comprising:
  producing an antibody raised against a chemokine receptor CCX-CKR polypeptide;
  determining the ability of the antibody to inhibit cancerous cell metastasis; and
  identifying the antibody as an agent capable of inhibiting cancerous metastasis.

Certain embodiments of the present disclosure provide an antibody and/or an antigen binding fragment thereof identified using a screening method as described herein.

Examples of cancerous cells are as described herein. In certain embodiments, the cancerous cell is a melanoma cell, a breast cancer cell, a prostate cancer cell, an ovarian cancer cell, or a colorectal cancer cell.

In certain embodiments, the chemokine receptor CCX-CKR polypeptide is a polypeptide as described herein. In certain embodiments, the chemokine receptor CCX-CKR polypeptide is an isolated polypeptide consisting of one or more of amino acid sequences SEQ ID NO.5 to SEQ ID NO.24, or a variant or a fragment thereof.

Certain embodiments of the present disclosure provide a kit for performing a method as described herein.

Certain embodiments provide a kit comprising an inhibitor of a chemokine receptor CCX-CKR. In certain embodiments, the inhibitor is an antibody and/or an antigen binding fragment thereof as described herein.

Standard techniques may be used for recombinant DNA technology, oligonucleotide synthesis, antibody production, peptide synthesis, tissue culture and transfection. Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), herein incorporated by reference.

Recitation of ranges of values herein are merely intended to serve as a shorthand method of referring individually to each separate value falling within the range, unless otherwise indicated herein, and each separate value is incorporated into the specification as if it were individually recited herein. Where a specific range of values is provided, it is understood that each intervening value, to the tenth of the unit of the lower limit unless the context clearly dictates otherwise, between the upper and lower limit of that range and any other stated or intervening value in that stated range, is included therein. All smaller sub ranges are also included. The upper and lower limits of these smaller ranges are also included therein, subject to any specifically excluded limit in the stated range.

Certain exemplary embodiments are illustrated by some of the following examples. It is to be understood that the following description is for the purpose of describing particular embodiments only and is not intended to be limiting with respect to the above description.

EXAMPLE 1

RNAi of CCX-CKR in B16 Melanoma Cells Results in Complete Rejection of Melanoma shRNA cassettes targeting CCX-CKR were inserted into lentiviral expression vector pLKO.1 purchased from Open Biosystems (Thermo Scientific) and siRNA produced according to the manufacturer's instructions. Lentiviral supernatants were produced by transfecting HEK293T packaging cells with one of the CCX-CKR shRNA or control shRNA-encoding lentiviral vectors together with psPAX2, pREV and pMD2-G packaging plasmids. The lentivirus-containing medium was harvested 48 hours post-transfection and placed onto B16 cells. After a 6-hour incubation the viral supernatant was removed and replaced with complete medium. The transductants were selected with puromycin for at least 2 weeks before being subjected to further analysis.

Mice were inoculated via the subcutaneous route with either control B16 cells (B16CTLkd), or B16 cells in which CCX-CKR had been knocked down by RNAi (designated B16CCXkd6 or kd7). CCX-CKR kd #6: 5'-CCGGCAG-TACGAAGTGATCTGCATACTCGAGTATGCAGAT-CACTTCGTACTG TTTTT-3' (SEQ ID NO. 2); CCX-CKR kd#7:5'-CCGGCTGCGATATGAGCAAACGCATCTCGA-GATGCGTTTGCTCATATCGCA GTTTTT-3' (SEQ ID NO. 4).

Tumour growth was measured on a daily basis for up to 22 days. The tumours were removed and examined by dissection microscopy. Graphs represent mean±sem (n=minimum of 10 mice per group). Dissected tumours are from one experiment.

The results are shown in FIG. 1. The data shows that a reduction in CCX-CKR activity results in a complete rejection of melanoma growth, as compared to mice inoculated with control B16 cells.

EXAMPLE 2

RNAi Knockdown of CCX-CKR Inhibits Metastasis of B16 Melanoma

Mice were inoculated with $4 \times 10^5$ cells via the footpad with either control B16 cells (B16GFPkd) or B16 cells in which CCX-CKR had been knocked down by RNAi (B16CCXkd6 or kd7). Pelvic lymph nodes (PLN) were collected and homogenate cultures grown in the presence of puromycin.

Figure 2:
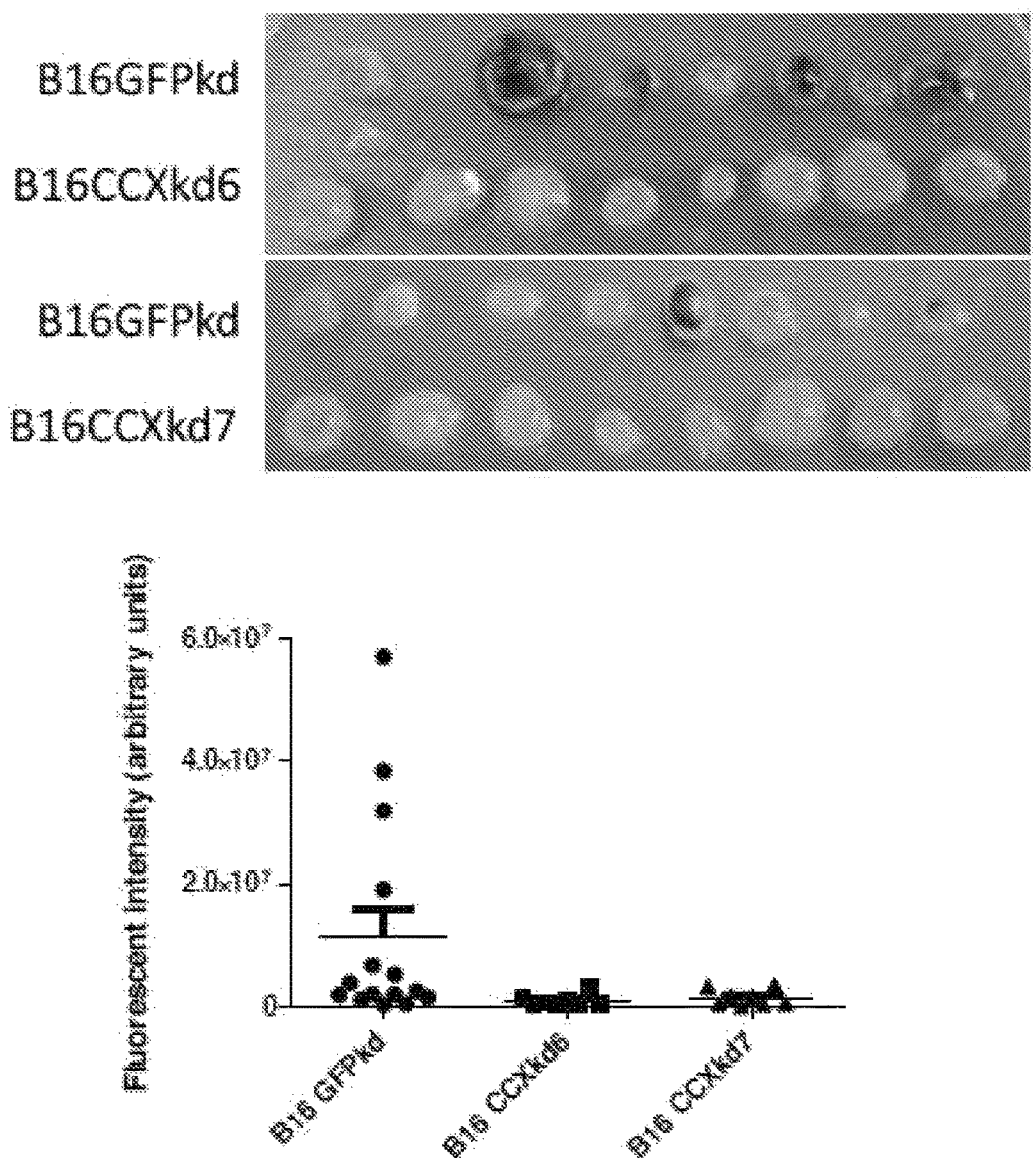
FIG. 2 shows RNAi knockdown of CCX-CKR inhibits lymphatic metastasis of B16 melanoma cells in mice inoculated with the cells.

The results are shown in FIG. 2. Knockdown of CCX-CKR dramatically inhibited the number of puromycin cells present in the PLN, demonstrating that RNAi knockdown inhibits lymphatic metastasis of B16 melanoma cells.

EXAMPLE 3

Loss of CCX-CKR Results in the Generation of an Anti-Melanoma Immune Response

Mice were injected with either control B16 cells or cells in which CCX-CKR had been knocked down by RNAi (B16CCXkd) and tumours were collected on the indicated days and analysed for the presence of various immune cells and cytokines. Where appropriate, data are expressed as mean±sem (n=minimum of 5 mice).

Figure 3:
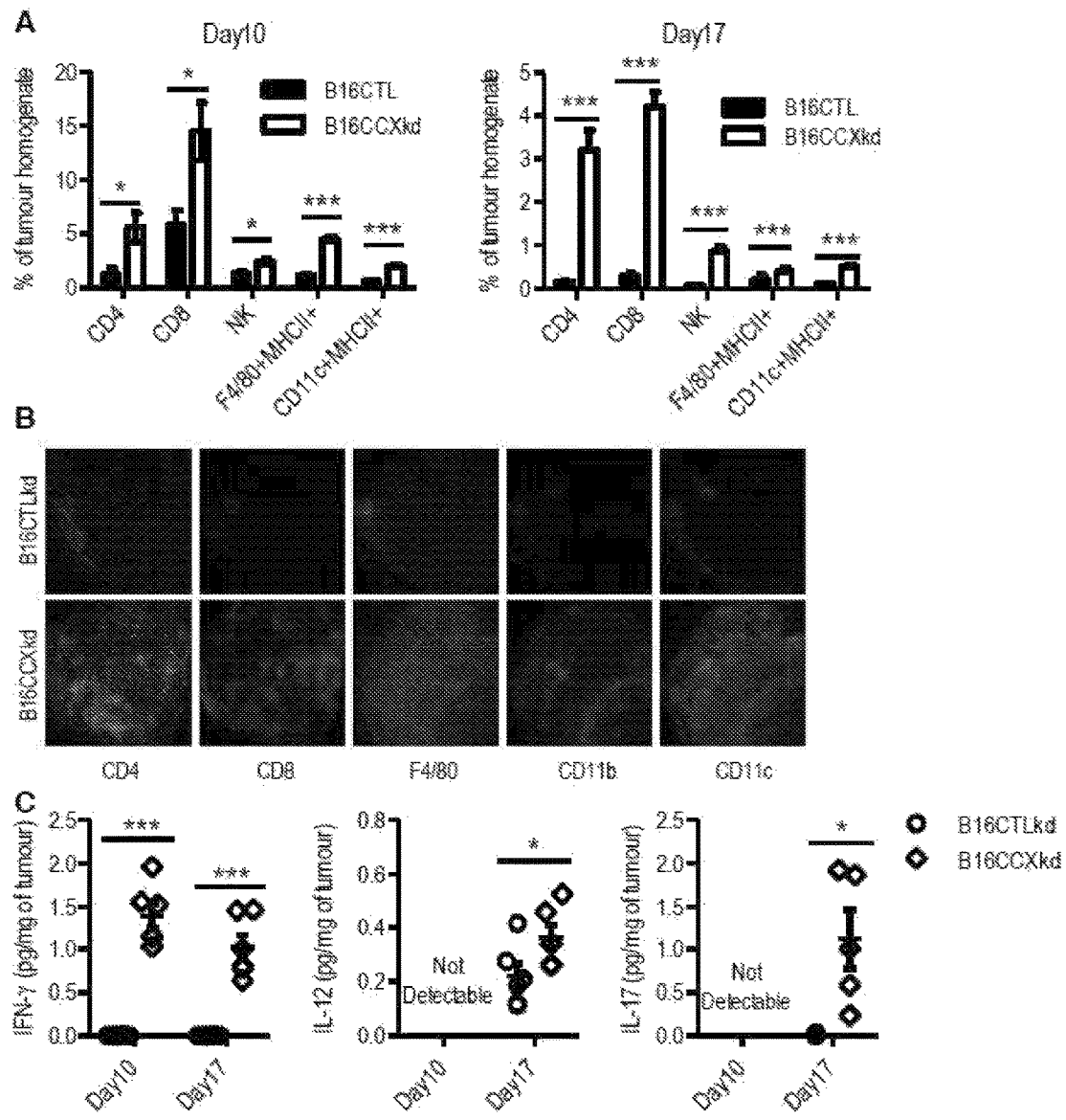
FIG. 3 shows loss of CCX-CKR results in the generation of an anti-melanoma immune response.

The results are shown in FIG. 3. FIG. 3A—Levels of tumour infiltrating leukocytes in CCX-CKR knockdown B16 tumours. The subcutaneous tumours harvested on day 10 or 17 post-tumour injection were minced and digested using collagenase IA. Erythrocytes were removed from the single cell suspension before Fcγ receptors were blocked and the cells were labelled for combinations of CD4 and CD8, CD49b and NK1.1, IA/IE and CD11c, or IA/IE and F4/80. Each point represents the data from individual mice and bars represent the mean±SEM of 6 mice per group. Statistical analysis was performed using unpaired t-test. FIG. 3B—Immunofluorescent staining of CCX-CKR knockdown tumour sections for tumour infiltrating leukocytes. The subcutaneous tumours harvested on day 17 post-tumour injection were embedded into OCT and frozen in liquid nitrogen. The tumour sections were fixed and blocked with 2% normal mouse serum and 2% normal goat serum. The sections were then stained for CD4, CD8, F4/80, CD11b or CD11c. Images were acquired using Leica SP5 spectral scanning confocal microscope and LAS AF software. Shown are representative images from 2 independent experiments, each performed with 3 mice per group. FIG. 3C—Levels of inflammatory cytokines in the CCX-CKR knockdown B16 tumour microenvironment. The subcutaneous tumours harvested from mice were minced and digested using collagenase IA. The homogenate supernatant was tested to measure the levels of IFN-γ, IL-12 and IL-17 by sequential ELISA. Concentrations of chemokines were normalised to each tumour weight. Each point represents the data from individual mice and bars represent the mean±SEM of 6 mice per group. Statistical analysis was performed using unpaired t-test.

EXAMPLE 4

CCX-CKR Knockout Mice are Resistant to Melanoma Growth and Metastasis

CCX-CKR$^{-/-}$ mice, generated at the Beatson Institute for Cancer Research (Glasgow, UK), and were backcrossed to the C57Bl/6 background for over 10 generations and were confirmed to be syngeneic to the C57Bl/6 strain using a genome-wide single nucleotide polymorphism (SNP) analysis eliminating the possibility of minor antigens differing between wt and knockout mice.

Figure 4:
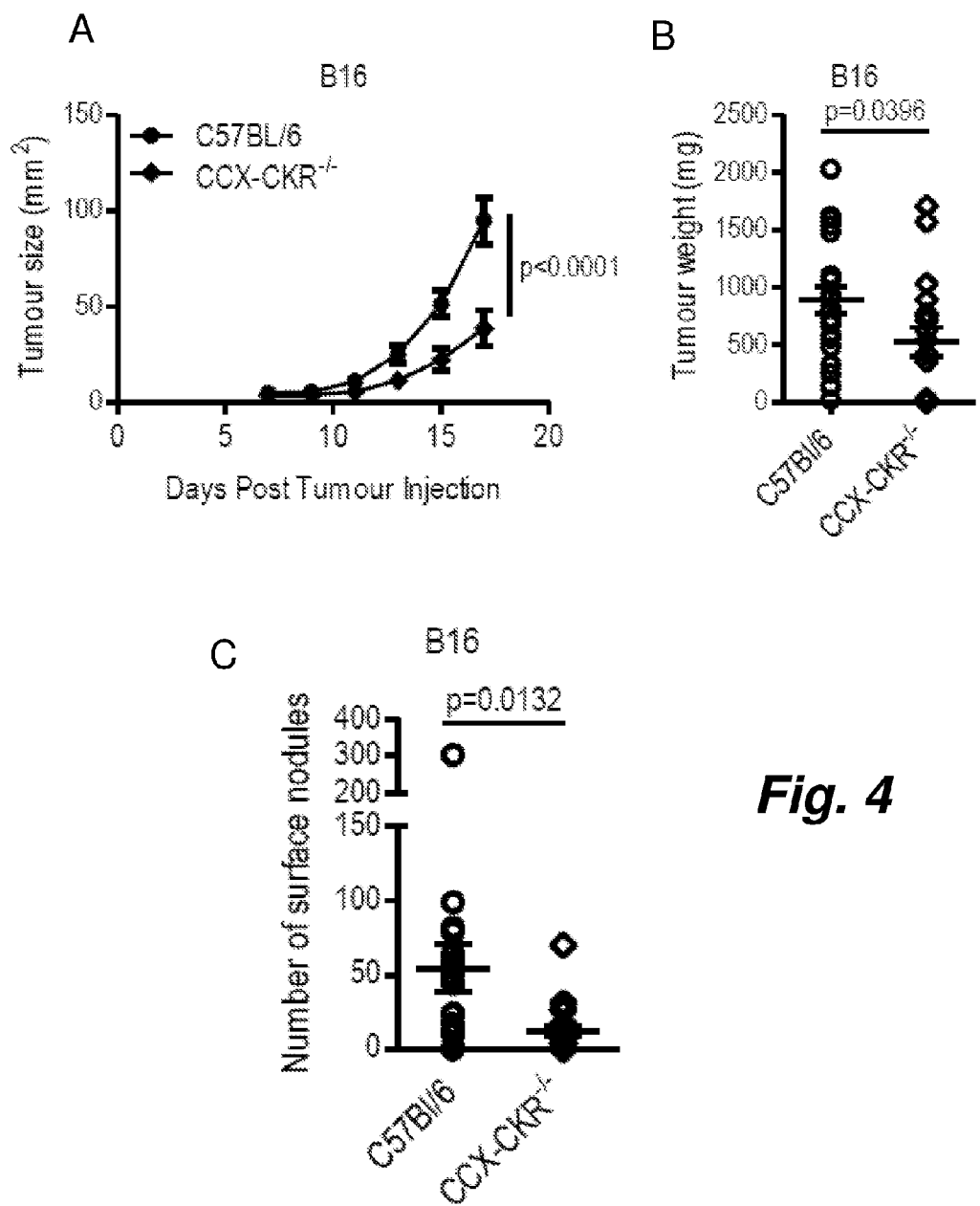
FIG. 4 shows CCX-CKR knockout mice are resistant to melanoma growth and metastasis.

CCX-CKR KO or WT mice were inoculated subcutaneously with WT B16 melanoma cells. Tumour growth was assessed daily and tumour weight was assessed at termination of the experiment. The results are shown in FIGS. 4A and 4B. Data are plotted as mean±sem (n=minimum 20 mice). Tumour size and tumour weight were markedly decreased in the CCX-CKR knock-out mice.

CCX-CKR KO or WT mice were inoculated intravenously with WT B16 melanoma cells. The lungs were collected 14 days later and the number of surface tumour nodules were quantified. The results are shown in FIG. 4C. Data are plotted as mean±sem (n=minimum 20 mice). The number of surface nodules is markedly decreased in CCX-CKR knock-out mice.

EXAMPLE 5

Effect of Anti-CCX-CKR (Anti-CCR11) Antibodies on Lung Colonisation by B16 Melanoma Cells Rabbits were immunized with one of the following peptides; MALELNQSAEYYYEENEMNY (SEQ ID NO.11; corresponding to amino acids 1-20 of the mouse CCX-CKR receptor; Genbank Accession No. AY072796) or THDYSQYEVICIKEEVRQFAK (SEQ ID NO.12; corresponding to amino acids 21-41 of the mouse CCX-CKR receptor; Genbank Accession No. AY072796) and the antibodies were purified from the serum using affinity column. The antibodies against two peptides were pooled before being injected into mice.

Figure 5:
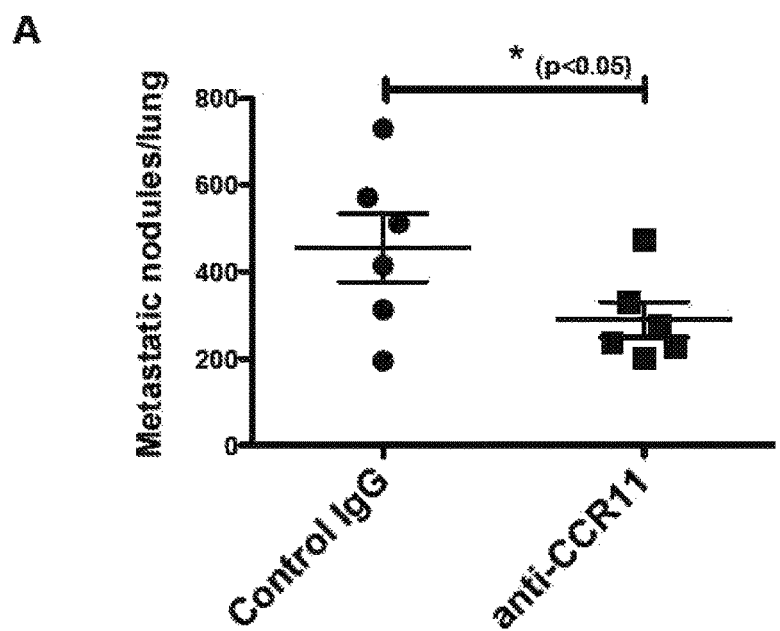
FIG. 5 shows the effect of anti-CCX-CKR antibodies on lung colonisation by B16 melanoma cells.
Figure 5:
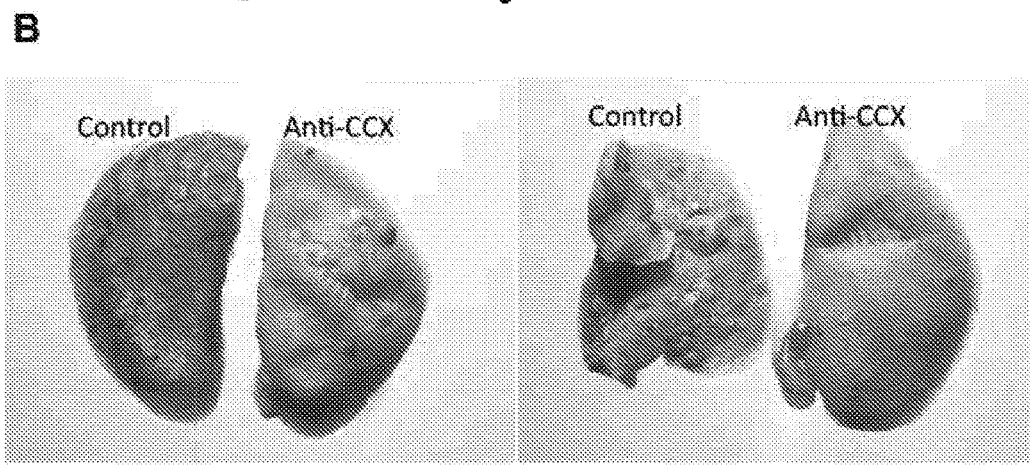

C57B16 mice were injected with 2×10$^5$ wild-type B16 melanoma cells by the intravenous route. Mice were either treated with 375 ug of normal rabbit IgG or affinity-purified anti-CCX-CKR polyclonal antibodies on days 0, 4 & 8. Lungs were excised 13 days later and the number of metastatic nodules was counted, as shown in FIG. 5A. Representative photographs are shown in FIG. 5B.

Treatment with anti-CCX-CKR antibodies reduced the number of metastatic nodules by approximately 40%. This was statistically significant at –<0.05 (1-tailed Student's T test, n=6 mice/group).

EXAMPLE 6

CCX-CKR Knockout Mice are Resistant to Breast Cancer Growth and Metastasis

Figure 6:
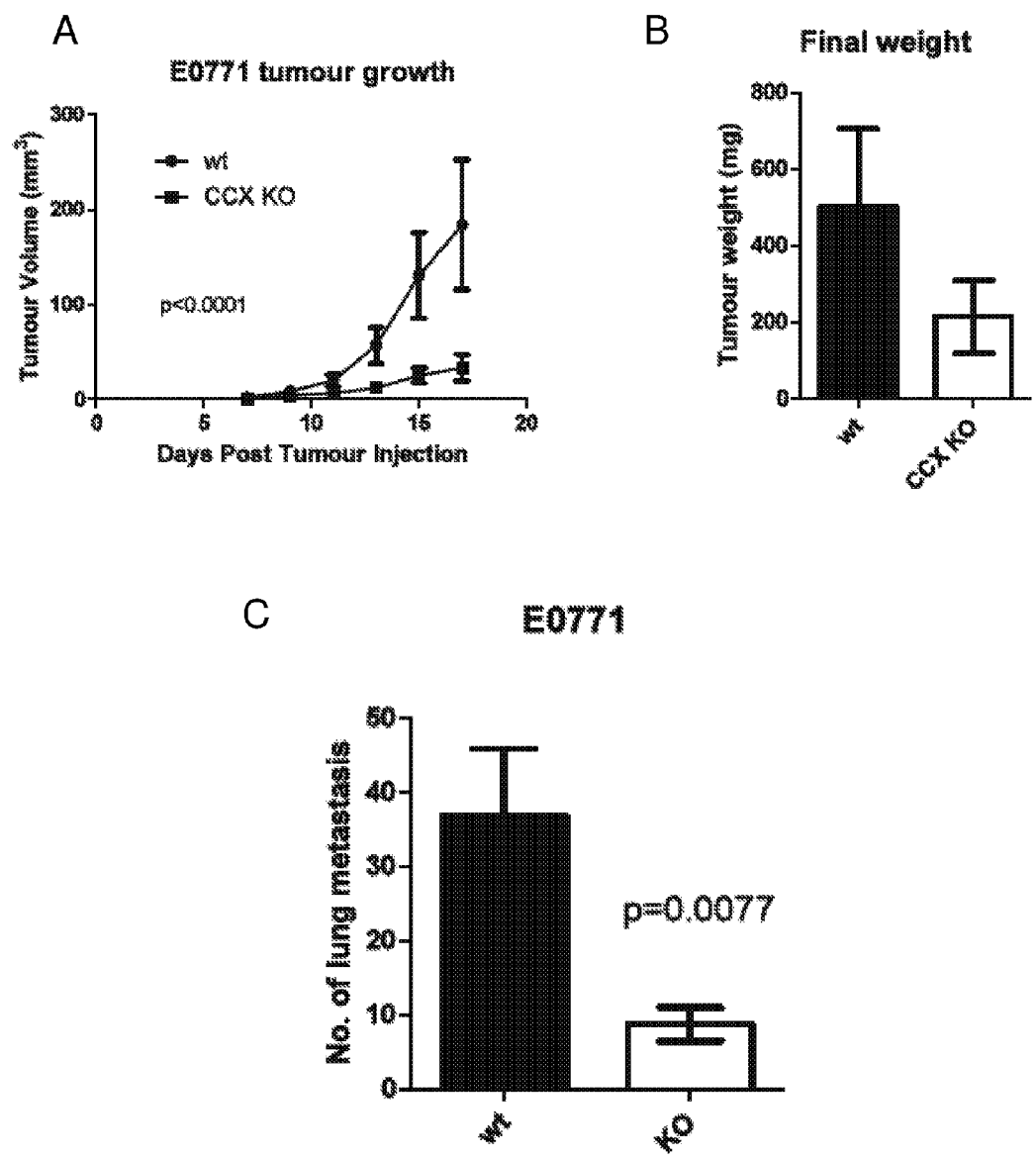
FIG. 6 shows CCX-CKR knockout mice are resistant to breast cancer growth and metastasis. (A) Effect on tumour volume. (B) Effect on tumour weight. C. Effect on lung metastases.

CCX-CKR KO or WT mice were inoculated subcutaneously with WT E0771 breast cancer cells. Tumour growth was assessed daily and tumour weight was assessed at termination of the experiment. The results are shown in FIG. 6A. Data are plotted as mean±sem (n=minimum 20 mice). As can be seen, tumour volume (FIG. 6A) and weight (FIG. 6B) were dramatically decreased in the CCX-CKR knock-out mice.

FIG. 6C shows that the number of lung metastases was dramatically decreased in CCX-CKR knock-out mice.

EXAMPLE 7

Figure 7:
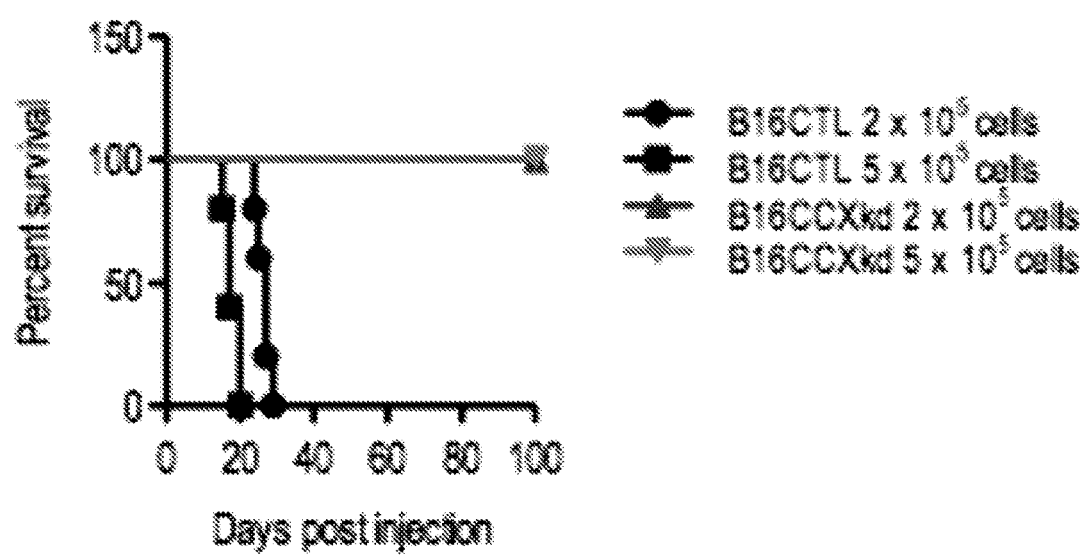
FIG. 7 shows that knockdown of CCX-CKR on B16 melanoma cells restores survival in mice inoculated with melanoma cells.

Knockdown of CCX-CKR on B16 Melanoma Cells Inhibits Metastasis and Restores Survival C57Bl/6 mice were injected with control or CCX-CKR knockdown cells at the indicated concentration (2×10$^5$ or 5×10$^5$ cells) via the intravenous route and survival was monitored over a 100 day period. The data is shown in FIG. 7. Knockdown of CCX-CKR on B16 melanoma cells restores survival of mice inoculated as compared to inoculation of control cells.

As used herein, the singular forms "a," "an," and "the" may refer to plural articles unless specifically stated otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

All methods described herein can be performed in any suitable order unless indicated otherwise herein or clearly contradicted by context. The use of any and all examples, or exemplary language (e.g., "such as") provided herein, is intended merely to better illuminate the example embodiments and does not pose a limitation on the scope of the claimed invention unless otherwise claimed. No language in the specification should be construed as indicating any non-claimed element as essential.

The description provided herein is in relation to several embodiments which may share common characteristics and features. It is to be understood that one or more features of one embodiment may be combinable with one or more features of the other embodiments. In addition, a single feature or combination of features of the embodiments may constitute additional embodiments.

The subject headings used herein are included only for the ease of reference of the reader and should not be used to limit the subject matter found throughout the disclosure or the claims. The subject headings should not be used in construing the scope of the claims or the claim limitations.

Although the present disclosure has been described with reference to particular examples, it will be appreciated by those skilled in the art that the disclosure may be embodied in many other forms.

Future patent applications may be filed on the basis of the present application, for example by claiming priority from the present application, by claiming a divisional status and/or by claiming a continuation status. It is to be understood that the following claims are provided by way of example only, and are not intended to limit the scope of what may be claimed in any such future application. Nor should the claims be considered to limit the understanding of (or exclude other understandings of) the present disclosure. Features may be added to or omitted from the example claims at a later date.

The invention claimed is:

1. A method of preventing and/or treating metastatic cancer in a subject, the method comprising administering to the subject a therapeutically effective amount of an inhibitor of a chemokine receptor CCX-CKR.

2. The method according to claim 1, wherein the metastatic cancer is a metastatic melanoma, metastatic breast cancer, metastatic prostate cancer, metastatic ovarian cancer, or metastatic colorectal cancer.

3. The method according to claim 1, wherein the inhibitor comprises one or more of a small interfering RNA, a microRNA, an antisense RNA, a ligand for a chemokine receptor CCX-CKR, and an antibody and/or an antigen binding part thereof.

4. The method according to claim 3, wherein the antibody and/or the antigen binding part thereof binds to one or more amino acids and/or an epitope located in one or more of the following regions of the human chemokine receptor CCX-CKR: amino acids 1 to 42, amino acids 109 to 113, amino acids 176 to 201, and amino acids 262 to 289, or an equivalent region of the receptor in another species.

5. The method according to claim 4, wherein the antibody and/or the antigen binding part thereof binds to an one or more amino acids and/or an epitope in one or more of polypeptide sequences: SEQ ID NOs. 5 to 24.

6. The method according to claim 1, wherein administering the inhibitor to the subject induces an immune response to the cancer in the subject.

7. The method according to claim 6, wherein administering the inhibitor to the subject induces anti-tumour CD4+ and/or CD8+ cells in the subject.

8. The method according to claim 4, wherein the antibody and/or the antigen binding part thereof binds to one or more amino acids and/or an epitope located in amino acids 1 to 42 of the human chemokine receptor CCX-CKR.

\* \* \* \* \*

```
                            SEQUENCE LISTING

<160> NUMBER OF SEQ ID NOS: 24

<210> SEQ ID NO 1
<211> LENGTH: 21
<212> TYPE: DNA
<213> ORGANISM: Artificial Sequence
<220> FEATURE:
<223> OTHER INFORMATION: small interfering RNA

<400> SEQUENCE: 1
tatgcagatc acttcgtact g                                                   21

<210> SEQ ID NO 2
<211> LENGTH: 57
<212> TYPE: DNA
<213> ORGANISM: Artificial Sequence
<220> FEATURE:
<223> OTHER INFORMATION: small interfering RNA

<400> SEQUENCE: 2
ccggcagtac gaagtgatct gcatactcga gtatgcagat cacttcgtac tgttttt           57

<210> SEQ ID NO 3
<211> LENGTH: 21
<212> TYPE: DNA
<213> ORGANISM: Artificial Sequence
<220> FEATURE:
<223> OTHER INFORMATION: smal interfering RNA

<400> SEQUENCE: 3
atgcgtttgc tcatatcgca g                                                   21

<210> SEQ ID NO 4
<211> LENGTH: 57
<212> TYPE: DNA
<213> ORGANISM: Artificial Sequence
<220> FEATURE:
<223> OTHER INFORMATION: small interfering RNA

<400> SEQUENCE: 4
ccggctgcga tatgagcaaa cgcatctcga gatgcgtttg ctcatatcgc agttttt           57

<210> SEQ ID NO 5
<211> LENGTH: 42
<212> TYPE: PRT
<213> ORGANISM: Homo sapiens

<400> SEQUENCE: 5

Met Ala Leu Glu Gln Asn Gln Ser Thr Asp Tyr Tyr Glu Glu Asn
1               5                   10                  15

Glu Met Asn Gly Thr Tyr Asp Tyr Ser Gln Tyr Glu Leu Ile Cys Ile
            20                  25                  30

Lys Glu Asp Val Arg Glu Phe Ala Lys Val
        35                  40

<210> SEQ ID NO 6
<211> LENGTH: 20
<212> TYPE: PRT
<213> ORGANISM: Homo sapiens

<400> SEQUENCE: 6
```

```
Met Ala Leu Glu Gln Asn Gln Ser Thr Asp Tyr Tyr Tyr Glu Glu Asn
1               5                   10                  15

Glu Met Asn Gly
            20

<210> SEQ ID NO 7
<211> LENGTH: 21
<212> TYPE: PRT
<213> ORGANISM: Homo sapiens

<400> SEQUENCE: 7

Thr Tyr Asp Tyr Ser Gln Tyr Glu Leu Ile Cys Ile Lys Glu Asp Val
1               5                   10                  15

Arg Glu Phe Ala Lys
            20

<210> SEQ ID NO 8
<211> LENGTH: 5
<212> TYPE: PRT
<213> ORGANISM: Homo sapiens

<400> SEQUENCE: 8

Lys Ile Met Cys Lys
1               5

<210> SEQ ID NO 9
<211> LENGTH: 25
<212> TYPE: PRT
<213> ORGANISM: Homo sapiens

<400> SEQUENCE: 9

Tyr Thr Val Asn Asp Asn Ala Arg Cys Ile Pro Ile Phe Pro Arg Tyr
1               5                   10                  15

Leu Gly Thr Ser Met Lys Ala Leu Ile
            20                  25

<210> SEQ ID NO 10
<211> LENGTH: 28
<212> TYPE: PRT
<213> ORGANISM: Homo sapiens

<400> SEQUENCE: 10

Cys Arg Ala Ile Asp Ile Ile Tyr Ser Leu Ile Thr Ser Cys Asn Met
1               5                   10                  15

Ser Lys Arg Met Asp Ile Ala Ile Gln Val Thr Glu
            20                  25

<210> SEQ ID NO 11
<211> LENGTH: 20
<212> TYPE: PRT
<213> ORGANISM: Mus musculus

<400> SEQUENCE: 11

Met Ala Leu Glu Leu Asn Gln Ser Ala Glu Tyr Tyr Tyr Glu Glu Asn
1               5                   10                  15

Glu Met Asn Tyr
            20

<210> SEQ ID NO 12
<211> LENGTH: 21
<212> TYPE: PRT
<213> ORGANISM: Mus musculus
```

```
<400> SEQUENCE: 12

Thr His Asp Tyr Ser Gln Tyr Glu Val Ile Cys Ile Lys Glu Val
1               5                   10                  15

Arg Gln Phe Ala Lys
            20

<210> SEQ ID NO 13
<211> LENGTH: 12
<212> TYPE: PRT
<213> ORGANISM: Mus musculus

<400> SEQUENCE: 13

Met Ala Leu Glu Leu Asn Gln Ser Ala Glu Tyr Tyr
1               5                   10

<210> SEQ ID NO 14
<211> LENGTH: 12
<212> TYPE: PRT
<213> ORGANISM: Mus musculus

<400> SEQUENCE: 14

Asn Tyr Thr His Asp Tyr Ser Gln Tyr Glu Val Ile
1               5                   10

<210> SEQ ID NO 15
<211> LENGTH: 12
<212> TYPE: PRT
<213> ORGANISM: Mus musculus

<400> SEQUENCE: 15

Asn Ala Val His Gly Trp Ile Leu Gly Lys Met Met
1               5                   10

<210> SEQ ID NO 16
<211> LENGTH: 12
<212> TYPE: PRT
<213> ORGANISM: Mus musculus

<400> SEQUENCE: 16

Gln Asn Ala Arg Cys Thr Pro Ile Phe Pro His His
1               5                   10

<210> SEQ ID NO 17
<211> LENGTH: 12
<212> TYPE: PRT
<213> ORGANISM: Mus musculus

<400> SEQUENCE: 17

Pro Ile Phe Pro His His Leu Gly Thr Ser Leu Lys
1               5                   10

<210> SEQ ID NO 18
<211> LENGTH: 12
<212> TYPE: PRT
<213> ORGANISM: Mus musculus

<400> SEQUENCE: 18

Asp Met Ser Lys Arg Met Asp Val Ala Ile Gln Val
1               5                   10

<210> SEQ ID NO 19
<211> LENGTH: 12
<212> TYPE: PRT
```

```
<213> ORGANISM: Homo sapiens

<400> SEQUENCE: 19

Met Ala Leu Glu Gln Asn Gln Ser Thr Asp Tyr Tyr
1               5                   10

<210> SEQ ID NO 20
<211> LENGTH: 12
<212> TYPE: PRT
<213> ORGANISM: Homo sapiens

<400> SEQUENCE: 20

Asn Gly Thr Tyr Asp Tyr Ser Gln Tyr Glu Leu Ile
1               5                   10

<210> SEQ ID NO 21
<211> LENGTH: 12
<212> TYPE: PRT
<213> ORGANISM: Homo sapiens

<400> SEQUENCE: 21

Asn Ala Val His Gly Trp Val Leu Gly Lys Ile Met
1               5                   10

<210> SEQ ID NO 22
<211> LENGTH: 12
<212> TYPE: PRT
<213> ORGANISM: Homo sapiens

<400> SEQUENCE: 22

Asp Asn Ala Arg Cys Ile Pro Ile Phe Pro Arg Tyr
1               5                   10

<210> SEQ ID NO 23
<211> LENGTH: 12
<212> TYPE: PRT
<213> ORGANISM: Homo sapiens

<400> SEQUENCE: 23

Pro Ile Phe Pro Arg Tyr Leu Gly Thr Ser Met Lys
1               5                   10

<210> SEQ ID NO 24
<211> LENGTH: 12
<212> TYPE: PRT
<213> ORGANISM: Homo sapiens

<400> SEQUENCE: 24

Asn Met Ser Lys Arg Met Asp Ile Ala Ile Gln Val
1               5                   10
```